United States Patent [19]

Kanios et al.

[11] Patent Number: 5,719,197
[45] Date of Patent: Feb. 17, 1998

[54] COMPOSITIONS AND METHODS FOR TOPICAL ADMINISTRATION OF PHARMACEUTICALLY ACTIVE AGENTS

[75] Inventors: David P. Kanios, Miami; Joseph A. Gentile, Plantation; Juan A. Mantelle; Steven Sablotsky, both of Miami, all of Fla.

[73] Assignee: Noven Pharmaceuticals, Inc., Miami, Fla.

[21] Appl. No.: 477,361

[22] Filed: Jun. 7, 1995

Related U.S. Application Data

[63] Continuation-in-part of Ser. No. 112,330, Aug. 27, 1993, Pat. No. 5,446,070, which is a continuation-in-part of Ser. No. 813,196, Dec. 23, 1991, Pat. No. 5,234,957, which is a continuation-in-part of Ser. No. 661,827, Feb. 27, 1991, abandoned, said Ser. No. 477,361, Jun. 7, 1995, is a continuation-in-part of Ser. No. 67,001, May 26, 1993, which is a continuation of Ser. No. 671,709, Apr. 2, 1991, Pat. No. 5,300,291, which is a continuation-in-part of Ser. No. 295,847, Jan. 11, 1989, Pat. No. 4,994,267, which is a continuation-in-part of Ser. No. 164,482, Mar. 4, 1988, Pat. No. 4,814,168.

[51] Int. Cl.$^6$ .............................. A61K 47/32; A61K 9/70
[52] U.S. Cl. .................... 514/772.6; 514/781; 514/782; 424/435; 424/443
[58] Field of Search ................... 424/449, 435, 424/443, 447, 450; 514/772.6, 781–782, 818, 947

[56] References Cited

U.S. PATENT DOCUMENTS

| | | | |
|---|---|---|---|
| 3,948,262 | 4/1976 | Zaffaroni | 128/260 |
| 4,144,317 | 3/1979 | Higuchi et al. | 424/427 |
| 4,379,454 | 4/1983 | Campbell et al. | 604/897 |
| 4,391,797 | 7/1983 | Folkman et al. | 424/425 |
| 4,421,737 | 12/1983 | Ito et al. | 424/449 |
| 4,624,665 | 11/1986 | Nuwayser | 604/307 |
| 4,661,099 | 4/1987 | von Bittera et al. | 604/290 |
| 4,675,009 | 6/1987 | Hymes | 604/304 |
| 4,751,087 | 6/1988 | Wick | 424/449 |
| 4,814,168 | 3/1989 | Sablotsky | 424/449 |
| 4,994,267 | 2/1991 | Sablotsky | 424/449 |
| 5,234,957 | 8/1993 | Mantelle | 514/772.6 |
| 5,300,291 | 4/1994 | Sablotsky | 424/78.18 |
| 5,446,070 | 8/1995 | Mantelle | 514/772.6 |
| 5,474,783 | 12/1995 | Miranda et al. | 424/448 |

FOREIGN PATENT DOCUMENTS

| | | |
|---|---|---|
| 0139127 | 8/1984 | European Pat. Off. . |
| 0 250 187 A2 | 12/1987 | European Pat. Off. . |
| 0 363 224 A1 | 4/1990 | European Pat. Off. . |
| 0 598 606 A1 | 11/1993 | European Pat. Off. . |
| 2 479 002 | 10/1981 | France . |
| 30 39 540 A1 | 5/1981 | Germany . |
| 217 989 A1 | 1/1985 | Germany . |
| 62-230716 | 10/1987 | Japan . |
| 62-230717 | 10/1987 | Japan . |
| 52460 | 6/1966 | Luxembourg . |
| 1126849 | 9/1968 | United Kingdom . |
| 2073588 | 10/1981 | United Kingdom . |
| WO 89/10740 | 11/1989 | WIPO . |
| WO 91/14463 | 10/1991 | WIPO . |
| WO 92/15289 | 9/1992 | WIPO . |
| WO 95/01766 | 1/1995 | WIPO . |

OTHER PUBLICATIONS

Japanese Abstract 57–181,020.

Primary Examiner—Carlos A. Azpuru
Attorney, Agent, or Firm—Foley & Lardner

[57] ABSTRACT

Compositions for topical application comprising a therapeutically effective amount of a pharmaceutical agent(s), a pharmaceutically acceptable bioadhesive carrier, a solvent for the pharmaceutical agent(s) in the carrier and a clay, and methods of administering the pharmaceutical agents to a mammal are disclosed.

27 Claims, No Drawings

COMPOSITIONS AND METHODS FOR TOPICAL ADMINISTRATION OF PHARMACEUTICALLY ACTIVE AGENTS

CROSS-REFERENCE TO RELATED APPLICATIONS

This application is a continuation-in-part of U.S. patent application Ser. No. 08/112,330, filed Aug. 27, 1993, now U.S. Pat. No. 5,446,070, which is a continuation-in-part of PCT/US92/01730, filed Feb. 27, 1992, which is a continuation-in-part application of U.S. patent application Ser. No. 07/813,196, filed Dec. 23, 1991, now issued as U.S. Pat. No. 5,234,957, which is a continuation-in-part of U.S. patent application Ser. No. 07/661,827 filed Feb. 27, 1991 and now abandoned. This application is also a continuation-in-part of copending U.S. patent application Ser. No. 08/067,001, filed May 26, 1993, which is a continuation of U.S. patent application Ser. No. 07/671,709, filed Apr. 2, 1991, now U.S. Pat. No. 5,300,291, which is a continuation-in-part of U.S. patent application Ser. No. 07/295,847, filed Jan. 11, 1989, now issued as U.S. Pat. No. 4,994,267, which is a continuation-in-part of U.S. patent application Ser. No. 07/164,482, filed Mar. 4, 1988, now issued as U.S. Pat. No. 4,814,168. The disclosures of all of said patents and patent applications are hereby incorporated by reference.

BACKGROUND OF THE INVENTION

1. Field of the Invention

The present invention relates to compositions and methods for the topical administration of pharmaceutically active agents to a mammal in need thereof. More particularly, the present invention relates to anesthesia and local anesthetic agents for topical administration. Still more particularly, the invention relates to a method for the topical administration of an anesthetic agent or a combination of anesthetic agents to prevent or ameliorate pain.

There is no limitation on the type of pharmaceutical agent that can be used in the present invention, provided that it can be absorbed topically, typically percutaneously. Thus, the pharmaceutical agent includes both drugs that are topically applied for local effects and those which can be administered topically for systemic effects.

2. Description of Background Art

Anesthetic agents are pharmacologically active agents that block nerve conduction when applied in therapeutically effective amounts. They can be used for local or systemic application. Anesthetic agents have been used extensively in the medical field to obtain topical anesthesia. The term "topical" or "topically" is used here in its coventional sense as referring to a spot, which can be in or on any part of the body, including but not limited to the epidermis, any other dermis, or any other body tissue. Topical administration or application means the direct contact of the anesthetic with tissue, such as skin or membrane, particularly the oral or buccal mucosa. Topical administration also includes application to hardened tissue such as teeth and appendages of the skin such as nails and hair. Previous methods of applying topical anesthetic agents to the skin or mucosa have used "non-finite" or liquid or semi-liquid carriers such as gels, lotions, emulsions, creams, plasters, or ointments, or "finite" carriers, non-spreading substances which retain their form, e.g. patches, dressings and bandages.

Local anesthetics generally are esters or amides of benzoic acid derivatives, administered either as the free base or the acid-addition salt. Free bases tend to be irritating at high concentrations. Acid-addition salts have low skin permeability.

To be effective, a topical, local anesthetic should contain sufficient concentration of the active agent to produce an anesthetic effect, it should penetrate the tissue such as intact skin or mucosa sufficiently to deliver a therapeutic dose, and it should exhibit rapid onset of anesthetic action and have a prolonged anesthetic effect. In achieving the foregoing, it is often desirable to have the anesthetic agent present in a high concentration to effect a rapid onset and, additionally or alternatively, in excess of the amount that can be immediately absorbed through the dermis at the site of application, so as to prolong anesthesia. On the other hand, the presence of the anesthetic agent primarily in crystalline form may irritate sensitive tissues such as mucosal tissues. This is particularly true with regard to lidocaine.

U.S. Ser. No. 08/112,330, now U.S. Pat. No. 5,446,070, granted Aug. 27, 1993, discloses and claims a drug in bioadhesive containing a solvent for the drug and a plasticizer for the bioadhesive. It has surprisingly been found that incorporation of a clay into the composition increased its cohesiveness.

SUMMARY OF THE INVENTION

The invention relates to a flexible, finite, bioadhesive composition for topical application comprising:
  (a) a therapeutically effective amount of at least one pharmaceutically active agent;
  (b) a pharmaceutically acceptable solvent for the pharmaceutically active agent and a plasticizer;
  (c) in admixture with the pharmaceutically active agent in the solvent, a pharmaceutically acceptable bioadhesive carrier in an amount from about 20 to about 50 weight percent based on the weight of the whole composition; and
  (d) a cohesiveness increasing amount of a clay;
wherein the composition is substantially free of water, substantially water insoluble and is a bioadhesive; and wherein the pharmaceutically active agent is present in non-crystallized form in the composition.

These compositions may further comprise a backing material which conforms to the size and shape of a single dosage of the composition.

This invention also relates to a method of administering the foregoing compositions.

The invention relates to method of administering one or more pharmaceutically active agents in a bioadhesive to a subject comprising the steps of:
  (a) providing a flexible, finite, bioadhesive composition for topical application comprising a therapeutically effective amount of at least one pharmaceutically active agent;
    a pharmaceutically acceptable solvent for the pharmaceutically active agent, and a plasticizer;
    in admixture with the pharmaceutically active agent in the solvent, a pharmaceutically acceptable polysaccharide bioadhesive, preferably a polysaccharide bioadhesive, carrier in an amount from about 20 to about 50 weight percent based on the weight of the whole composition; and a cohesiveness increasing amount of a clay;
    wherein the composition is substantially free of water, substantially water insoluble and is a bioadhesive; and wherein the pharmaceutically active agent is present in non-crystallized form in the composition; and
  (b) contacting an area of skin or mucous membrane with the composition to administer the pharmaceutically active agent.

DETAILED DESCRIPTION OF THE INVENTION

This invention provides a composition which when administered topically, for example to an area of the skin, skin appendage, teeth or mucosa, delivers a pharmaceutical agent or a combination of agents to produce a local or systemic effect over a prolonged period of time.

In accordance with one embodiment of the present invention, a pharmaceutically acive agent and a plasticizer for the adhesive are in admixture with a pharmaceutically acceptable adhesive, which is preferably a bioadhesive, and more preferably a polysaccharide bioadhesive, and a cohesiveness increasing amount of clay, is provided in a finite, flexible form for topical application to the skin or dermal membrane of a mammal. Preferably, the pharmaceutically active agent is in solid form at ambient temperatures and pressures.

In accordance with a further embodiment of the present invention, a combination of local anesthetic agents, a solvent for the anesthetic agents and a finite or non-finite, fluid or flexible, pharmaceutically acceptable carrier is provided for topical application to a tissue, for example the skin or mucosa of a mammal.

The anesthetic agents of this invention are those known, or of a type known, in the art. The local anesthetic bases encompassed by this invention are weak organic bases which are lipophilic in nature and thus poorly soluble in water. However, these bases will react with organic or inorganic acids to form acidic, water soluble acid addition salts. Thus, the term "base" as used herein means the un-ionized form of the anesthetic that can furnish an electron pair to form a covalent bond. The term "acid" as used herein is a substance that can take up an electron pair to form a covalent bond. The term "salt" as used herein means the form produced by a base, for example an anesthetic base, upon its reaction with an organic or inorganic acid.

The base form and the salt form of the anesthetic agent incorporated in the present combination composition are desirably different anesthetic agents to achieve maximum duration of the combined anesthetic effect. By the term "different" is meant that the salt form in any combination is not a salt of the base form used in the given combination.

Local anesthetic agents suitable for use in the practice of this invention include amides and esters. Examples of the amides are lidocaine, prilocaine, mepivacaine, bupivacaine, dibucaine and etidocaine. Esters include procaine, tetracaine, propoxycaine, chloroprocaine, benzocaine, butamben picrate, cocaine, hexylcaine, piperocaine, oxyprocaine and proparacaine. Other suitable local anesthetics for use in the practice of this invention include cyclomethycaine, dimethisoquin, ketocaine, diperodon, dyclonine and pramoxine, all typically administered in the form of the acid addition hydrochloride or sulfate salts.

The acid-addition salts of the present invention are any non-toxic, pharmaceutically acceptable organic or inorganic salts. Typical inorganic salts are the hydrogen halides, especially the hydrochlorides, carbonates, borates, phosphates, sulfates, hydrogen sulfates, hydrobromides, nitrates, sulfides, and arsenates. Typical organic salts are salts of mono- and polycarboxylic acids such as the citrate, tartrate, malate, cinnamate, oxalate, formate, succinate and phthalates. The term "non-salicylate" used herein means that in certain embodiments, the acid addition salts do not include salts of esters of salicylic acid and its analogs such as aspririn.

The solvents for the finite and non-finite forms of the active agents are non-toxic, pharmaceutically acceptable substances, preferably liquids, which do not substantially negatively affect the adhesion properties or solubility of the system. The solvent is preferably a polyhydric alcohol or combination of polyhydric alcohols. The term polyhydric alcohol means any organic polyalcohol and includes dipropylene glycol, propylene glycol, polyethylene glycol, glycerin, butylene glycol, hexylene glycol, polyoxyethylene, polypropylene glycol, sorbitol, ethylene glycol, and the like. Other suitable solvents include fatty acids such as oleic acid, linoleic acid, capric acid and the like, as well as fatty esters or alcohols. Further suitable solvents include other non-toxic, non-volatile solvents commonly used in dermal or transdermal compositions for dissolving like compounds.

The above mentioned polyhydric alcohols may include those having 2 to 6 alcoholic hydroxyl groups. Such polyhydric alcohols include glycols, triols and polyols having 4 to 6 alcoholic hydroxyl groups. Typical of said glycols are glycols containing 2 to 6 carbon atoms, e.g. ethylene glycol, propylene glycol, butylene glycol, polyethylene glycol (average molecular weight about 200–8,000, preferably about 200 to 6,000), etc. Examples of said triols include glycerin, trimethylolpropane, etc. Said polyols are exemplified by sorbitol (sorbit), polyvinylpyrrolidone, etc. These polyhydric alcohols may be used either singly or in combination (preferably, of two or three). Thus, for example, glycerin alone or a mixture of glycerin and butylene glycol is employed.

Among those polyhydric alcohols, those which satisfy the requirements relevant to the adjustment and maintenance of softness of the external surface of the invention, the compatibility or co-dispersibility with the other components, and provide a proper consistency of the composition, may be freely used. Those which are low in volatility are generally preferred and, in this regard, dipropylene glycol, glycerin, propylene glycol, butylene glycol, and sorbitol are appropriate solvents, according to the invention.

Although the exact amount of the polyhydric alcohols in the composition depends on the nature of other components, and therefore cannot be stated in general terms, the proportion may range from about 5 to about 50 weight percent based on the whole composition, and depending on the amount of other ingredients.

In one embodiment, the solvent is in an amount from about 20 to 50 weight percent based on the weight of the whole composition. The solvent includes from about 5% to about 50%, and more preferably about 10% to 30% of a solvent known to plasticize the bioadhesive carrier. A particularly useful plasticizer is glycerine.

The addition of clay has been found to improve cohesiveness of the bioadhesive in transdermal formulations without reducing the rate of drug delivery. Suitable clays include kaolinites such as boalinite, anauxite, dickite and nacrite, montmorillonites such as montmorillonite, bentonite, bordellite and montronite, illites/muscovites such as illite and glauconite, chlorites, polygorshites such as attapulgite, halloysite, metabolloysite, allophane and aluminum silicate clays. Especially useful are smectite clays. The use of metal oxides such as magnesium oxide, zinc oxide, and titanium oxide with the clay tends to increase the cohesiveness of the preparation.

The clay is used in a cohesiveness increasing amount, namely about 0.5 to about 20%, preferably about 0.5 to about 10%, and more preferably, about 1 to about 7%, of the total composition. The metal oxides are conveniently used in amounts from about 0.1 to about 1%, but can be used in greater or lesser amounts. The addition of clay is based on the surprising finding that the addition of a clay to a bioadhesive results in an increase in viscosity, swelling and gelling of the adhesive matrix such that it permits reduction of the amount of bioadhesive on greater than a weight for weight basis.

The high concentrations of microdispersed active agent of this invention are achieved typically by mixing the agents with the solvent, preferably at an elevated temperature, for example about 70° to 100° C., to obtain a mixture, preferably a solution, of the agents which is then added to the pharmaceutically acceptable carrier.

The term "microdispersed" is intended to mean that in the solvent, and subsequently the carrier, there is an intimate dispersion of the pharmaceutically active agent at the molecular or ionic level, such that crystals of the pharmaceutically active agent cannot be detected using a microscope having a magnification of 25×. As such, the pharmaceutically active agent is in "non-crystallized" form when in the compositions of the present invention.

Preferably the pharmaceutically active agent is substantially dissolved in the solvent so that when mixed with the finite adhesive or non-finite fluid carrier, the agent is microdispersed in the composition.

Solvent selection for the active agents depends on the form of the active agent, namely whether it is in free base form or acid-addition salt form. Solvents for the salt form of active agents are polar organic solvents. Polar organic solvents are preferably polyhydric alcohols, as discussed above. Various other solvents suitable for either the base or acid-addition form of the active agent are those solvents known to dissolve either or both of these two types of forms including cyclic ketones such as 2-pyrrolidone; N-(2-hydroxyethyl) pyrrolidone, N-methylpyrrolidone, 1-dodecylazacycloheptan2-one and other n-substituted alkyl-azacycloalkyl-2-ones (azones) dimethylformadide, and dimethylsulfoxide. Other suitable solvents for the free base form of the active agent are cell envelope disordering compounds known to be useful in topical pharmaceutical preparations, which compounds are thought to assist in skin penetration by disordering the lipid structure of the stratum corneum cell-envelopes. Some of these compounds are generally encompassed by the formula:

R—X wherein R is a straight-chain alkyl of about 7 to 16 carbon atoms, a non-terminal alkenyl of about 7 to 22 carbon atoms, or a branched-chain alkyl of from about 13 to 22 carbon atoms, and X is —OH, —COOCH$_3$, —COOC$_2$H$_5$, —OCOCH$_3$, —SOCH$_3$, —P(CH$_3$)$_2$O, —COOCH$_2$H$_4$OC$_2$H$_4$OH, —COOCH(CHOH)$_4$CH$_2$OH, —COOCH$_2$CHOHCH$_3$, —COOCH$_2$CH(OR") CH$_2$)R". —(OCH$_2$CH$_2$)$_m$OH, —COOR ', or —CONR'$_2$ where R; is —H, —CH$_3$, —C$_2$H$_5$, —C$_3$H$_7$ OR —C$_2$H$_4$OH; R" is —H, or a non-terminal alkenyl of about 7 to 22 carbon atoms; and m is a positive integer from 2 to 6; provided that when R" is an alkenyl and X is —OH or —COOH, at least one double bond is in the cis-configuration.

It has been discovered that high concentrations of a combination of microdispersed active agents, namely up to 50% by weight of the optionally finite, flexible composition, require the use of a solvent as herein described. In one embodiment of the invention, the active agent(s) is in an amount of from 10 to 40 weight percent based on the weight of the total composition. Omission of the solvent in the procedure of Example 1 below yields a product filled with crystals or a crystalline mass.

In particularly preferred embodiments of this invention, the active agent is an anesthetic. Preferably, it is a free base and salt form of an anesthetic. The free base local anesthetic agent is selected from the group comprising lidocaine, procaine, propoxycaine, mepivacaine, prilocaine, dyclonine, pramoxine, benzocaine and chloroprocaine. The salt form is preferably one selected from the group comprising prilocaine, tetracaine, bupivacaine, dyclonine, dibucaine, etidocaine and lidocaine salts. The aforementioned bases and salts can be used alone or in combination with other anesthetic bases and salts as needed to achieve therapeutically effective levels when administered transdermally, or through other topical route.

The term "therapeutically effective amount" is intended to mean the amount of drug sufficient to produce an anesthetic effect when applied topically. These amounts are known in the art or may be determined by methods known in the art, and typically range from about 1 to 20,000 mg per human adult and preferably about 10 to 10,000 mg and most preferably range from about 20 to 5,000 mg of the anesthetic agent per application, depending upon the anesthetic agents chosen, and whether the tissue, such as the skin or mucous membrane is the site of action. The only upper limit on the amount of anesthetic in the composition is that the preparation is substantially free of crystals of anesthetic agent and the amount of solvent used is not sufficient to undesirably affect the adhesive properties of the finite composition. Thus, the single ingredient anesthetic agent contains a therapeutically effective amount of anesthetic agent within the foregoing range.

The concentration as well as the quantity of anesthetic per unit area, namely per square or cubic centimeter can be varied independently in order to achieve the desired effect. Higher concentrations of anesthetic base contained in a dosage form of decreased thickness will result in an anesthetic with fast onset and short duration. High concentrations of the anesthetic base contained in a dosage form of increased thickness (higher mg of anesthetic per square or cubic centimeter) will result in potent anesthesia with fast onset and long duration. Low concentrations of the anesthetic base in a dosage form of decreased thickness will result in mild anesthesia with longer onset and short duration. Low concentrations of the anesthetic base contained in a dosage form of increased thickness will have mild anesthesia with longer onset and longer duration. As shown in the above explanation, the ability to vary the concentration of anesthetic from very low (about 1%) to high (40% or higher) of the total composition, when combined with the ability to coat thin (about 0.001 inches) or thick (about 0.500 or more inches) enables the practitioner of the invention to vary the dosage of the system as needed for particular anatomical sites of interest.

As a general rule, in the case of a given tissue, e.g. the mucosal application, the anesthetic drug selected, the concentration and thickness and the duration of the application is determined based upon the anesthetic's ability to penetrate the tissue, for example mucosa, and to be at peak effectiveness within about 2 to 30 minutes. The duration of the effect of the anesthetic on the tissue, for example the oral mucosa, should range between about 2 to 240 minutes, depending on the anesthetic agent selected, the concentration of the anesthetic and the thickness of application. Longer or shorter durations can also be selected dependent on need, as will be apparent to one skilled in the art.

The ratio of the free base form to the salt form in the composition of this invention will depend on several factors, namely: (1) the identity of the salt and base used; (2) the desired duration of action; and (3) the desired rapidity of anesthetic effect. As a general rule in the case of mucosal application, the ratios of base to salt are such that the free base form preferably should penetrate the mucosa and be at its peak effectiveness within about a 2 to 30 minute period, whereas, the salt form should preferably penetrate the mucosa and be at its peak effectiveness within a period of about 10 to 75 minutes. The duration of the effect of these on the oral mucosa will range between about 2 to 240 minutes depending on the base/salt combination selected and the length of application time. In practice to achieve this effect, the amount by weight base form will be in excess of the amount by weight of the salt form.

The term "onset of anesthesia" is intended to mean the time to peak effect on the individual nerves. Onset of anesthesia principally depends upon the lipid solubility, molecular size, and quantity of available, un-ionized form of the local anesthetic. Thus, anesthetics with a high lipid solubility or a low $pK_a$, or both, have a more rapid onset of anesthesia.

The term "duration of anesthesia" as used herein means the period of time during which the local anesthetic measurably blocks nerve conduction. The foregoing depends upon all of the factors listed for onset of anesthesia, as well as on the extent of protein binding of the anesthetic agent.

The anesthetic agent free base can penetrate intact skin to a limited degree, and will more rapidly penetrate the skin if the keratin layers are abraded. In the case of the oral mucosa, the anesthetic base will penetrate much more readily due to the different keratin composition and the resulting difference in the hydrophilicity as compared to the stratum corneum of intact skin.

As a general rule, the salt forms of the aforementioned anesthetics do not appreciably penetrate intact skin, but the un-ionized base form do penetrate to a limited degree. Both forms, salt and base, will penetrate abraded keratin layers. The salt as well as the base will penetrate, to a differing degree, the buccal mucosa due to the buccal mucosa's hydrophilicity, as compared to the stratum corneum of intact skin. Generally, the higher the lipid content of the mucosal membrane, the more rapidly the base form of the anesthetic agent will be absorbed. Therefore, when the composition is used for application to oral or buccal mucosa, the different lipid contents of the gum (gingiva) and the alveolar mucosa must be kept in mind in order to obtain the optimal penetration rate.

Although applicants do not intend to be bound by any theory or proposed mechanism of operation, it is believed that the base which is lipid soluble has a rapid onset of anesthesia since it enters the lipo-protein nerve membrane preventing the depolarization and ion exchange involved in stimulus conduction. On the other hand, the salt which is not lipid soluble, penetrates to the lipo-protein nerve membrane only after the buffering capacity of the skin or mucosal tissue converts the salt to the base, the final result being a delayed onset of anesthesia.

The salts of this invention are selected on the basis of onset of anesthesia and duration of anesthesia. Adjusting the ratio of base to salt affects the relative onset as well as the duration of anesthetic action. The greater the amount of anesthetic agent having a rapid onset of action, the shorter the onset of anesthesia. Similarly, the greater the amount of the anesthetic agent having a prolonged duration of anesthesia, the more prolonged the duration of anesthesia. More than two anesthetic agents may be used to have a broader spectrum of activity. Moreover, the composition can include other drugs used concomitantly.

Generally, the concentration of solubilized pharmaceutically active agent can range, on a weight basis, between about 1 and about 50%, preferably between about 2.5 and about 40% and more preferably between about 5 and about 30% of the total weight of the composition. In a preferred embodiment of the invention, the concentration of the dissolved drug is between about 5% and about 20% by weight of the total composition. The base used in the preferred embodiment for a single ingredient preparation is lidocaine.

Generally, for the combination of anesthetics, the ratio by weight of base to salt is about 90:10 to about 60:40, preferably about 75:25 to about 60:40, and more preferably about 70:30 to about 60:40. For other salts, the ratios are comparable based on relative molar amounts. Generally, the ratio by weight of base to salt is more than 1:1. In a preferred embodiment of the invention, the ratio is about 2:1 base to salt, respectively. The base used in the preferred embodiment is lidocaine and the preferred salt is a salt of prilocaine, bupivacaine, dyclonine, mepivacaine, or tetracaine, preferably the hydrochloride salt. Table 1 below summarizes the peak and duration of action of selected local anesthetics based primarily on application to skin or mucous membranes:

TABLE 1

| Local Anesthetic | Minimum Adult Dose | Maximum Adult Dose (mg) | Peak Effect (minutes) | Duration of Effect (minutes) |
|---|---|---|---|---|
| Dibucaine |  | 25 | <15 | 120–240 |
| Lidocaine |  | 750 | 2–5 | 30–60 |
| Benzocaine |  | 5000 | 1 | 30–60 |
| Cocaine |  | 50 | 2–5 | 30–120 |
| Tetracaine |  | 50 | 3–8 | 30–60 |
| Dyclonine |  | 100 | <10 | <60 |
| Pramoxine |  | 200 | 3–5 | NA |

NA: Not Available.
Source: Drug Facts and Comparisons, 1990 edition, J. B. Lippincott Company, St. Louis, MO. Page 601.

In general, the relative speed of onset of anesthesia and duration of anesthesia for any given form of anesthetic agent is available in the literature or can be calculated by standard tests.

Onset time, as well as duration of anesthesia, will vary from individual to individual as well as on the basis of the site of application. When applying the composition to highly keratinized dermal tissues, the onset of anesthesia may take as long as 2 to 4 hours.

The composition of this invention can be manufactured by numerous methods known in the art which permit the achievement of a microdispersed anesthetic agent, including extruding, molding, solvent casting, coating, and all other methods which employ a solvent to disperse the drug in a finite or non-finite carrier.

In one embodiment of the invention, the composition comprises a combination of a first anesthetic agent in the form of a base and a second anesthetic agent in the form of an acid-addition salt. In this embodiment, the term "pharmaceutically acceptable carrier" is intended to be any suitable finite or non-finite carrier including liquids, semi-liquids or solid carriers, such as a bioadhesive. Thus, the active agents may be admixed with a non-adhesive tape or other finite carrier or a carrier such as a cream, gel, emulsion, lotion, salve, paste, plaster, ointment, spray-solution, or any other "non-finite" carrier known in the art of pharmaceutical delivery. For example, the base of a non-finite carrier may be fatty oils, lanolin, vaseline, paraffins, glycols, higher fatty acids and higher alcohols.

Contrary to the typical method for manufacturing a drug in a solvent containing adhesive, the adhesive composition of this invention contains a non-volatile solvent. Thus the composition is either not dried to prevent removal of the solvent from the adhesive or a solvent is used at least part of which is not substantially evaporated during the conditions of manufacture. The composition in question can then be applied to a flexible backing or a combination of backings which will serve to define the size and shape of a single dosage of the composition. Such backing may be a three dimensional material such as paper, a non-woven fabric or a natural or synthetic polymer substance. Methods of coating backings are well-known in the art and include techniques involving Mayer rod, gravure, and knife-over roll. Further processing of backings may involve the use of converting equipment for die cutting.

The finished dosage form will be substantially occlusive to water permeation in in vivo.

For example, in one embodiment, the anesthetic agents are dissolved in a solvent, preferably a polyhydric alcohol, and then the resulting mixture is added to an adhesive prior to being placed onto the flexible form or backing. In another embodiment, the resulting mixture is an cream, gel, emulsion, lotion, salve, plaster, paste, ointment, spray-solution or other "non-finite" composition. The final form in which the composition of the invention will be applied depends upon the anatomical site of application and ease of access.

The phrase "flexible, finite, pharmaceutically acceptable carrier" is intended to mean a solid capable of conforming to a surface with which it comes into contact and which is capable of maintaining the contact so as to facilitate topical application without any adverse physiological response, and which can be used to establish the compositions herein in their preferred solid form without being appreciably decomposed by aqueous contact during administration to a patient.

An important characteristic of the embodiment of the present invention wherein a bioadhesive carrier is employed, relates to the substantially water-free and water-insoluble nature of the composition. By the term "substantially water-free" is meant that the preparation contains less than about 10% by weight water, and preferably less than about 5%, and most preferably less than about 3%. In general, it is desirable to avoid the addition of water entirely and to eliminate, as far as possible, the presence of water in the other ingredients of the composition. By the term "substantially water insoluble" is meant that the composition remains "finite" and does not generally detach from the skin, dermal membrane or other tissue at the site of application and under the conditions of regular, intended use for a period of at least 3 hours. The advantages to be derived from the substantially water-free and water-insoluble nature of the compositions of the present invention include achievement of higher concentrations of drug. Another advantage of these compositions is minimization of precipitation of drug, which precipitation affects processing of the composition, affects rate of delivery of the drugs and in certain cases can affect sensitivity of the subject to be treated to the drug.

Suitable adhesive carriers include any of the non-toxic polymers, particularly those of the type used to carry drugs for transdermal delivery including natural or synthetic elastomers, such as polyisobutylene, styrene, butadiene, styrene isoprene block copolymers, acrylics, urethanes, silicones, styrene butadiene copolymers, methyl acrylate copolymers, acrylic acid, polyacrylates, and polysacchrides such as, karaya gum, tragacanth gum, pectin, guar gum, cellulose, and cellulose derivatives such as methyl cellulose, propyl cellulose, cellulose acetate and the like, along with other substances known for use in transdermal preparations capable of forming a solid colloid that can adhere to tissue, used alone or in combination with other suitable carriers. A particularly preferred carrier is a bioadhesive for application to the dermis, preferably the mucosa.

The adhesive can be modified so as to adhere to the skin or mucosal tissue, depending on the intended application site. As stated above, preferred adhesives for application to the skin are bioadhesives.

The term "adhesive" as used herein means a substance, inorganic or organic, natural or synthetic, that is capable of surface attachment to the intended application site.

The term "bioadhesive" as used herein means an adhesive which attaches and preferably strongly attaches to a live or freshly killed biological surface such as skin or mucosal tissue upon hydration. Indeed, to qualify as a bioadhesive, a substance must be capable of maintaining adhesion in moist or wet in in vivo or in vitro environments. The final finite composition of the present invention is "self-adhesive" in that it attaches to the site of interest without the need to reinforce its attachment by way of another adhesive which is applied to a backing.

The strength of adherence can be measured by standard tests for measuring the force, e.g. in dynes per square centimeter, as disclosed in U.S. Pat. No. 4,615,697. Suitable bioadhesives include those prepared from optionally partially esterified polyacrylic acid polymers, including but not limited to, polyacrylic acid polymers lightly crosslinked with a polyalkenyl polyether such as those commercially available from B.F. Goodrich, Cincinnati, Ohio, under the trademarks Carbopol 934, 934P, 940 and 941.

Other suitable bioadhesives include natural or synthetic polysaccharides. The term "polysaccharide" as used herein means a carbohydrate decomposable by hydrolysis into two or more molecules of monosaccharides or their derivatives. Suitable polysaccharides include cellulose derivatives such as methylcellulose, cellulose acetate, carboxymethylcellulose, hydroxyethylcellulose and the like. Other suitable bioadhesives are pectin, a mixture of sulfated sucrose and aluminum hydroxide, hydrophilic polysaccharide gums such as natural plant exudates, including karaya gum, ghatti gum, tragacanth gum, xanthan gum, jaraya gum and the like, as well as seed gums such as guar gum, locust bean gum, psillium seed gum and the like. The term non-finite carrier refers to any liquid or semi liquid known for or suitable for use in pharmaceutical preparations as will be apparent to one skilled in the art.

In addition to the above ingredients, there may also be incorporated other additives selected from among the various pharmaceutically acceptable additives available to those skilled in the art. These additives include binders, stabilizers, preservatives, flavorings and pigments. In a preferred finite form embodiment, the compositions of the present invention also contain a binder such as lecithin which "binds" the other ingredients, thereby enhancing the uniform consistency of the final composition.

The composition is administered in appropriate sizes, typically having a surface area of from about 0.1 to about 200 $cm^2$ or conveniently 0.2 to 100 $cm^2$. The anesthetic agent is loaded into the composition in as high a concentration as necessary to effect therapy, e.g., in a range from about 0.1 $mg/cm^2$ to about 50 or more $mg/cm^2$ or 0.1 mg/ml to about 500 or more mg/ml when a non-finite carrier such as an ointment, gel, lotion, cream, paste, plaster, emulsion, or spray-solution is used.

In general, the composition can have the following types and amounts of ingredients:

| Ingredient | Typical Range (% by weight) | Preferred Range (% by weight) | Optimum Range (% by weight) |
|---|---|---|---|
| Finite Form | | | |
| Adhesive | 15 to 60 | 20 to 50 | 20 to 35 |
| Solvent(with plast.) | 2 to 75 | 5 to 70 | 20 to 40 |
| Drug(s) | 1 to 50 | 5 to 40 | 10 to 30 |
| Clay | 0.5 to 20 | 0.5 to 10 | 1 to 7 |

In one embodiment, the flexible, finite, bioadhesive composition for topical application comprises:

a therapeutically effective amount of at least one pharmaceutically active agent;

a pharmaceutically acceptable solvent for the pharmaceutically active agent, including a plasticizer for the bioadhesive, and a cohesiveness increasing amount of clay;

in admixture with the pharmaceutically active agent in the solvent, a pharmaceutically acceptable bioadhesive, preferably a polysaccharide bioadhesive, in an amount from about 20 to about 50 weight percent based on the weight of the whole composition;

wherein the composition is substantially water insoluble and self-adhesive; and wherein the pharmaceutically active agent is present in non-crystallized from in the composition.

The term "administering" is intended to mean any mode of application to a tissue which results in the physical contact of the composition with an anatomical site in need of anesthesia. The term "subject" is intended to include all warm-blooded mammals, preferably humans.

In one method of the invention wherein a bioadhesvie carrier is employed, the pharmaceutically acceptable solvent is in a preferred amount from about 20 to about 50 weight percent of which the plasticizer represents about 10 to 30 weight percent based on the weight of the whole composition, the bioadhesive carrier is in an amount from about 20 to about 50 weight percent and the clay represents about 0.5 to about 20% of the composition based on the weight of the whole composition. More preferably, the bioadhesive composition of this method is comprised of 20 to 40 weight percent of karaya gum, about 20 to 40 weight percent of at least one glycol, and about 10 to 25 weight percent of lidocaine base and 0.5 to 10% of clay, and is further comprised of a binder in an amount sufficient to bind the other ingredients.

In one embodiment, the composition of the invention comprises about 20 to 35 weight percent of karaya gum, about 20 to 40 weight percent of at least one glycol, about 10 to 25 weight percent of lidocaine base, and 1 to 7 percent smectite clay, and further comprising a binder in an amount sufficient to bind the other ingredients.

In another embodiment, the composition of the invention comprises about 10 weight percent of karaya gum, about 13 weight percent of at least one glycol, and about 8 weight percent of lidocaine base, and further comprising a binder in an amount sufficient to bind the other ingredients.

In another embodiment, the composition of the invention comprises about 7 weight percent of karaya gum, about 13 weight percent of at least one glycol, and about 8 weight percent of lidocaine base, and further comprising a binder in an amount sufficient to bind the other ingredients.

In another embodiment, the composition of the invention comprises about 5 weight percent of karaya gum, about 13 weight percent of at least one glycol, and about 8 weight percent of lidocaine base, 2 percent Bentonite, and further comprising a binder in an amount sufficient to bind the other ingredients.

In another embodiment, the composition of the invention comprises about 5 weight percent of karaya gum, about 13 weight percent of at least one glycol, and about 8 weight percent of lidocaine base, 2 percent Bentonite, and further comprising a binder in an amount sufficient to bind the other ingredients.

The following examples will further describe the instant invention, and are used for the purposes of illustration only, and should not be considered as limiting in any way the invention being disclosed herein. Percent (%) as used in these examples refer to percentage of the liquid formulation on a weight to weight basis and temperatures are given in degrees celsius (°C.).

EXAMPLE 1

| Ingredient | w/w % | | | |
|---|---|---|---|---|
| Lidocaine base | 8.0 | 8.0 | 8.0 | 8.0 |
| Dipropylene Glycol | 5.0 | 5.0 | 5.0 | 5.0 |
| 60% Lecithin in Propylene Glycol | 8.0 | 8.0 | 8.0 | 8.0 |
| Karaya Gum | 10.0 | 7.0 | 5.0 | 5.0 |
| Bentonite (Polargel NF*) | 0 | 0 | 2.0 | 2.0 |
| Zinc Oxide | 0 | 0 | 0 | 0.1 |
| Glycerin | 6.0 | 6.0 | 6.0 | 6.0 |

*Available from American Colloid Co.

The final product is manufactured by first blending the lidocaine base, the propylene glycol, lecithin, and glycerin at about 70° to 90° C. until all of the drug is dissolved. The solution is then cooled to 20° to 35° C. prior to adding the karaya gum and clay. Once the karaya gum and clay is added, the final composition are applied to a suitable backing material such as a non-woven, polyester film (for example, the film sold under the trademark Sontara 8100, manufactured by DuPont de Nemours, E.I. and Co., Wilmington, Del.) and warmed to about 100° C. to accelerate the formation of the gel into its final, finite form.

The foregoing examples are illustrative embodiments of the invention and are merely exemplary. A person skilled in the art may make variations and modification without departing from the spirit and scope of the invention. All such modifications and variations are intended to be included within the scope of the invention as described in this specification and the appended claims.

Indeed, the present invention is intended to encompass and be suitable for use by substituting any of the following drugs for the anesthetic agent as the pharmacologically active agent in the composition and methods for use of the same:

α-ADRENERGIC AGONIST such as Adrafinil, Adrenolone, Amidephrine, Apraclonidine, Budralazine, Clonidine, Cyclopentamine, Detomidine, Dimetofrine, Dipivefrin, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine, Methylhexaneamine, Metizolene, Midodrine, Naphazoline, Norepinephrine, Norfenefrine, Octodrine, Octopamine, Oxymetazoline, Phenylephrine, Phenylpropanolamine, Phenylpropylmethylamine, Pholedrine, Propylhexedrine, Pseudoephedrine, Rilmenidine, Synephrine, Tetrahydrozoline, Tiamenidine, Tramazoline, Tuaminoheptane, Tymazoline, Tyramine, Xylometazoline β-ADRENERGIC AGONIST such as Formoterol, Methoxyphenamine, Ritodrine, Terbuterol α-ADRENERGIC BLOCKER such as Dapiprazole, Doxazosin, Ergoloid Mesylates, Fenspiride, Prazosin, Terazosin, Tolazoline, Trimazosin, Yohimbine β-ADRENERGIC BLOCKER such as Acebutolol, Amosulalol, Arotinolol, Atenolol, Befunolol, Betaxolol, Bevantolol, Bisoprolol, Bopindolol, Bucumolol, Bufetolol, Bufuralol, Bunitrolol, Bupranolol, Butofilolol, Carazolol, Carteolol, Carvedilol, Celiprolol, Cetamolol, Cloranolol, Dilevalol, Epanolol, Esmolol, Indenolol, Labetalol, Levobunolol, Mepindolol, Metipranolol, Metoprolol, Moprolol, Nadolol, Nadoxolol, Nifenalol, Nipradilol, Oxprenolol, Penbutolol, Pindolol, Practolol, Propranolol, Sotalol, Sulfinalol, Talinolol, Tertatolol, Timolol, Toliprolol, Xibenolol ALCOHOL DETERRENT such as Calcium Cyanamide Citrated, Disulfiram, Nitrefazole ALDOSE REDUCTASE INHIBITOR such as Epalrestat, Ponalrestat, Sorbinil, Tolrestat ANABOLIC such as Androisoxazole, Androstenediol, Bolandiol, Bolasterone, Clostebol, Ethylestrenol, Formyldienolone, 4-Hydroxy-19-nortestosterone, Methandriol, Methenolone, Methyltrienolone, Nandrolone, Nandrolone Decanoate, Nandrolone p-Hexyloxyphenyl-propionate, Nandrolone Phenpropionate, Norbolethone, Oxymesterone, Quinbolone, Stenbolone, Trenbolone ANALGESIC (DENTAL) such as Chlorobutanol, Clove, Eugenol, potassium Nitrate, Potassium Oxalate ANALGESIC (NARCOTIC) such as Alfentanil, Allylprodine, Alphaprodine, Anileridine, Benzylmorphine, Bezitramide, Buprenorphine, Butorphanol, Clonitazene, Codeines, Desomorphine, Dextromoramide, Dezocine, Diampromide, Dihydrocodeine, Dihydrocodeinone Enol Acetate, Dihydromorphine, Dimenoxadol, Dimepheptanol, Dimethylthiambutene, Dioxaphetyl Butyrate, Dipipanone, Eptazocine, Ethoheptazine, Ethylmethlythiambutene, Ethylmorphine, Etonitazene, Fentanyl, Hydrocodone, Hydromorphone, Hydroxypethidine, Isomethadone, Ketobemidone, Levorphanol, Lofentanil, Meperidine, Meptazinol, Metazocine, Methadone, Metopon, Morphine, Morphine Derivatives, Myrophine, Nalbuphine, Narceine, Nicomorphine, Norlevorphanol, Normethadone, Normorphine, Norpipanone, Opium, Oxycodone, Oxymorphone, Papaveretum, Pentazocine, Phenadoxone, Phenazocine, Pheoperidine, Piminodine, Piritramide, Proheptazine, Promedol, Properidine, Propiram, Propoxyphene, Sufentanil, Tilidine ANALGESIC (NON-NARCOTIC) such as Acetaminophen, Acetaminosalol, Acetanilide, Acetylsalicylates, Acetylsalicylsalicylic Acid, Alclofenac, Alminoprofen, Aloxiprin, Aluminum Bis (acetylsalicylate), Aminochlorthenoxazin, 2Amino-4-picoline, Aminopropylon, Aminopyrine, Antipyrine, Antipyrine Salicylate, Antrafenine, Apazone, Aspirin, Benorylate, Benoxaprofen, Benzpiperylon, Benzydamine, p-Bromoacetanilide, 5-Bromosalicylic Acid Acetate, Bucetin, Bufexamac, Bumadizon, Butacetin, Carbamazepine, Carbetidine, Carbiphene, Carsalam, Chloralantipyrine, Chlorthenoxazin(e), Choline Salicylate, Cinchophen, Ciramadol, Clometacin, Cropropamide, Crotethamide, Dexoxadrol, Difenamizole, Diflunisal, Dipyrocetyl, Dipyrone, Emorfazone, Enfenamic Acid, Epirizole, Etersalate, Ethenzamide, Ethoxazene, Etodolac, Felbinac, Fenoprofen, Floctafenine, Flufenamic Acid, Fluoresone, Flupirtine, Fluproquazone, Flurbiprofen, Fosfosal, Gentisic Acid, Glafenine, Ibufenac, Imidazole Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Methotrimeprazine, Metofoline, Miroprofen, Morazone, Morpholine Salicylate, Naproxen, Nefopam, Nifenazone, 5' Nitro-2' propoxyacetanilide, Parsalmide, Perisoxal, Phenacetin, Phenazopyridine, Phenocoll, Phenopyrazone, Phenyl Acetylsalicylate, Phenyl Salicylate, Phenyramidol, Pipebuzone, Piperylone, Prodilidine, Propacetamol, Propyphenazone, Proxazole, Quinine Salicylate, Ramifenazone, Rimazolium Metilsulfate, Salacetamide, Salicin, Salicylamide, Salicylamide O-Acetic Acid, Salicylic Acid, Salicylates and Derivatives, Salicylsulfuric Acid, Salsalte, Salverine, Simetride, Sulfamipyrine, Suprofen, Talniflumate, Tenoxicam, Terofenamate, Tetradrine, Tinoridine, Tolfenamic Acid, Tolpronine, Tramadol, Viminol, Xenbucin, Zomepirac ANDROGEN such as Boldenone, Fluoxymesterone, Mestanolone, Mesterolone, Methandrostenolone, 17-Methyltestosterone, 17α-Methyl-testosterone 3-Cyclopentyl Enol Ether, Norethandrolone, Normethandrone, Oxandrolone, Oxymetholone, Prasterone, Stanlolone, Stanozolol, Testosterone, Testosterone 17-Chloral Hemiacetal, Testosterone 17β-Cypionate, Testosterone Enanthate, Testosterone Nicotinate, Testosterone Pheynylacetate, Testosterone Propionate, Tiomesterone ANESTHETIC such as Acetamidoeugenol, Alfadolone Acetate, Alfaxalone, Amucaine, Amolanone, Amylocaine, Benoxinate, Betoxycaine, Biphenamine, Bupivacaine, Burethamine, Butacaine, Butaben, Butanilicaine, Buthalital, Butoxycaine, Carticaine, 2-Chloroprocaine, Cocaethylene, Cocaine, Cyclomethycaine, Dibucaine, Dimethisoquin, Dimethocaine, Diperadon, Dyclonine, Ecgonidine, Ecgonine, Ethyl Aminobenzoate, Ethyl Chloride, Etidocaine, Etoxadrol, β-Eucaine, Euprocin, Fenalcomine, Fomocaine, Hexobarbital, Hexylcaine, Hydroxydione, Hydroxyprocaine, Hydroxytetracaine, Isobutyl p-Aminobenzoate, Kentamine, Leucinocaine Mesylate, Levoxadrol, Lidocaine, Mepivacaine, Meprylcaine, Metabutoxycaine, Methohexital, Methyl Chloride, Midazolam, Myrtecaine, Naepaine, Octacaine, Orthocaine, Oxethazaine, Parethoxycaine, Phenacaine, Phencyclidine, Phenol, Piperocaine, Piridocaine, Polidocanol, Pramoxine, Prilocaine, Procaine, Propanidid, Propanocaine, Proparacaine, Propipocaine, Propofol, Propoxycaine, Pseudococaine, Pyrrocaine, Risocaine, Salicyl Alcohol, Tetracaine, Thialbarbital, Thimylal, Thiobutabarbital, Thiopental, Tolycaine, Trimecaine, Zolamine ANOREXIC such as Aminorex, Amphecloral, Benzaphetamine, Chlorphentermine, Clobenzorex, Cloforex, Cyclexedrine, Diphemethoxidine, Fenbutrazate, Fenfluramine, Fenproporex, Furfurylmethylamphetamine, Levophacetoperate, Mefenorex, Metamfeproamone, Norpseudoephedrine, Phenpentermine, Picilorex ANTHELMINTIC (CESTODES) such as Arecoline, Aspidin, Aspidinol, Dichlorophen(e), Embelin, Kosin, Napthalene, Niclosamide, Pellertierine, Pellertierine Tannate, Quinacrine ANTHELMINTIC (NEMATODES) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dymanthine, Gentian Violet, 4-Hexylresorcinol, Kainic Acid, Mebendazole, 2-Napthol, Oxantel, Piperazines, Pyrantel, Pyrvinium Pamoate, α-Santonin, Stilbazium Iodide, Tetrachloroethylene, Thiabendazole, Thymol, Thymyl N-Isoamylcarbamate, Triclofenol Piperazine, Urea Stibamine ANTHELMINTIC (ONCHOCERCA) such as Ivermectin ANTHELMINTIC (SCHISTOSOMA) such as Amphotalide, Antimony(s) and Derivatives, Becanthone, Hycanthone, Lucanthone, Niridazole, Oxamniquine, Praziquantel, Stibocaptate, Stibophen ANTHELMINTIC (TREMATODES) such as Anthiolimine ANTIACNE such as Algestone Acetophenide, Azelaic Acid, Benzoyl Peroxide, Dichloroacetic Acid, Motretinide, Retinoic Acid, Tetroquinone ANTIALLERGIC such as Amlexanox, Astemizole, Azelastine, Cromolyn, Fenpiprane, Histamines, Ketotifen, Nedocromil, Oxatomide, Pentigetide, Poison Ivy Extract, Poison Oak Extract, Poison Sumac Extract, Repirinast, Tiaramide, Tranilast, Traxanox, Urushiol ANTIAMEBIC such as Arsthinol, Bialamicol, Carbarsone, Cephaeline, Chlorbetamide, Chlorphenoxamide, Dehydroemetine, Dibromopropamidine, Diloxanide, Dephetarsone, Emetine, Fumagillin, Glaucarubin, Glycobiarsol, 8-Hydroxy-7-iodo-5-quinolinesulfonic Acid, Iodochlorhydroxyquin, Iodoquinol, Paromomycin, Phanquinone, Phearsone Sulfoxylate, Polybenzarsol, Propamidine, Quinfamide, Secnidazole, Sulfarside, Teclozan, Thiocarbamizine, Thiocarbarsone, Tinidazole ANTIANDROGEN such as Bifluranol, Cyoctol, Cyproterone, Oxendolone ANTIANGINAL such as Amlodipine, Amyl Nitrite, Cinepazet Maleate, Imolamine, Isosorbide Dinitrate, Limaprost, Molsidomine, Nitroxyalklamide Derivatives ANTIARRHYTHMIC such as Acecaine, Adenosine, Ajmaline, Alprenolol, s-Aminoalkyl-s-Arylsulfoximines, Amoproxan, Aprindine, Bretylium Tosylate, Bubumolol, Bunaftine, Butidrine, Butobendine, Capobenic Acid, Cifenline, Disopyramide, Encainide, Flecainide, Hydroquinidine, Indecainide, Ipratropium, Lorajmine, Lorcainide, Meobentine, Mexiletine, Moricizine, Pirmenol, Prajmaline, Procainamide, Pronethalol, Propafenone, Pyrinoline, Quinidine, Quinidine Sulfate, Quinidine, Tocainide, Viquidil ANTIARTERIOSCLEROTIC such as Pyridinol Carbamate ANTIARTHRITIC/ANTIRHEUMATIC such as Allocupreide Sodium, Auranofin, Aurothioglucose, Aurothioglycanide, Azathioprine, Di-tert-Butylphenols, Calcium3-Aurothio-2propanol-1-sulfonate Clobuzarit, Cuproxoline, Diacerein, Glucosamine, Gold Sodium Thiomalate, Gold Sodium Thiosulfate, Hydroxychloroquine, Kebuzone, Lobenzarit, Melittin, Myoral, Penicillamine ANTIBACTERIAL (ANTIBIOTIC)
  Aminoglycosides such as Amikacin, Apramycin, Arbekacin, Bambermycins, Butirosin, Dibekacin, Dihdrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid, Tobramycin
  Amphenicols such as Azidamfenicol, Chloramphenicol, Chloramphenicol Palmitate, Chloramphenicol Pantothenate, Florfenicol, Thiamphenicol
  Ansamycins such as Rifamide, Rifampin, Rifamycin, Rifaximin
  β-Lactams
    Carbapenems such as Imipenem
    Cephalosporins such as 1-Carba (dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine, Pivcefalexin
    Cephamycins such as Cefbuperazone, Cefmetazole, Cefminox, Cefetan, Cefoxitin
    Monobactams such as Aztreonam, Carumonam, Tigemonam
    Oxacephems such as Flomoxef, Moxolactam
    Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillin N, Penicillin O, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin, Ticarcillin
  Lincosamides such as Clindamycin, Lincomycin
  Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin, Troleandomycin Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin, Zinc Bacitracin Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin, Tetracycline Others such as Cycloserine, Mupirocin, Tuberin,

ANTIBACTERIAL (SYNTHETIC)

2,4-Diaminopyrimidines such as Brodimoprim, Tetroxoprim, Trimethoprim

Nitrofurans such as Furaltadone, Furazolium, Nifuradene, Nifuratel, Nifurfoline, Nifurpirinol, Nifurprazine, Nifurtoinol, Nitrofurantoin Quinolones and Analogs such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin, Tosufloxacin Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, $N^2$-Formylsulfisomidine,$N^4$-β-D-Glucosylsulfanilamide, Mafenide, 4', -(Methyl-sulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, Sulfanilamidomethanesulfonic Acid Triethanolamine Salt, 4-Sulfanilamidosalicylic Acid, $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine, Sulfisoxazole Sulfones such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-Sulfonyldianiline-N,N' digalactoside, Sulfoxone, Thiazolsulfone Others such as Clofoctol, Hexedine, Magainins, Methenamine, Methenamine Anhydromethylenecitrate, Methenamine Hippurate, Methenamine Mandelate, Methenamine Sulfosalicylate, Nitroxoline, Squalamine, Xibornol ANTICHOLINERGIC such as Adiphenine, Alverine, Ambutonomium, Aminopentamide, Amixetrine, Amprotropine Phosphate, Anisotropine Methylbromide, Apoatropine, Atropine, Atropine N-Oxide, Benactyzine, Benapryzine, Benzetimide, Benzilonium, Benztropine Mesylate, Bevonium Methyl Sulfate, Biperiden, Butropium, N-Butylscopolammonium Bromide, Buzepide, Camylofine, Caramiphen, Chlorbenzoxamine, Chlorphenoxamine, Cimetropium, Clidinium, Cyclodrine, Cyclonium, Cyclopentolate, Cycrimine, Deptropine, Dexetimide, Dibutoline Sulfate, Dicyclomine, Diethazine, Difemerine, Dihexyverine, Diphemanil Methylsulfate, N-(1,2-Diphenylethyl) nicotinamide, Dipiproverine, Diponium, Emepronium, Endobenzyline, Ethopropazine, Ethybenztropine, Ethylbenzhydramine, Etomidoline, Eucatropine, Fenpiverinium, Fentonium, Flutropium, Glycopyrrolate, Heteronium, Hexocyclium Methyl Sulfate, Homatropine, Homatropine Methyl Bromide, Hyoscyamine, Ipratropium, Isopropamide, Levomepate, Mecloxamine, Mepenzolate, Metcaraphen, Methantheline, Methixen, Methscopolamine, Octamylamine, Oxybutynin, Oxyphencyclimine, Oxyphenonium, Pentapiperide, Penthienate, Phencarbamide, Phenglutarimide, Pipenzolate, Piperidolate, Piperilate, Poldine Methysulfate, Pridinol, Prifinium, Procyclidine, Propantheline, Propenzolate, Propyromazine, Scopolamine N-Oxide, Stilonium, Stramonium, Sultroponium, Thihexinol, Thiphenamil, Tiemonium, Timepidium, Tiquizium, Tridihexethyl Iodide, Trihexyphenidyl Hydrochloride, Tropacine, Tropenzile, Tropicamide, Trospium, Valethamate, Xenytropium ANTICONVULSANT such as Acetylpheneturide, Albutoin, Aloxidone, Aminoglutethimide, 4-Amino-3-hydroxybutyric Acid, Atrolactamide, Beclamide, Buramate, Carbamazepine, Cinromide, Clonazepam, Decimemide, Diethadione, Dimethadione, Doxenitoin, Eterobarb, Ethadione, Ethosuximide, Ethotoin, Fluoresone, 5-Hydroxytryptophan, Lamotrigine, Magnesium Sulfate, Mephenytoin, Metharbital, Methetoin, Methsuximide, 5-Methyl-5-(3-phenanthryl)-hydantoin, 3-Methyl-5-phenylhydantoin, Narcobarbital, Nimetazepam, Nitrazepam, Paramethadione, Phenacemide, Pheneturide, Phensuximide, Phenytoin, Phethenylate Sodium, Primidone, Progabide, Solanum, Strontium, Suclofenide, Sulthiame, Tetrantoin, Trimethadione, Valproic Acid, Valpromide, Vigabatrin, Zonisamide

ANTIDEPRESSANT

Bicyclics such as Binedaline, Caroxazone, Citalopram, Dimethazan, Indalpine, Fencamine, Indeloxazine, Nefopam, Nomifensine, Oxitriptan, Oxypertine, Paroxetine, Sertraline, Thiazesim, Trazodone, Zometapine Hydrazides/Hydrazines such as Benmoxine, Iproclozide, Iproniazid, Isocarboxazid, Nialamide, Octamoxin, Phenelzine Pyrrolidones such as Cotinine, Rolicyprine, Rolipram Tetracyclics such as Maprotiline, Metralindole, Mianserin, Oxaprotiline Tricyclics such as Adinazolam, Amitriptyline, Amitriptylinoxide, Amoxapine, Butriptyline, Clomipramine, Demexiptiline, Desipramine, Dibenzepin, Dimetracrine, Dothiepin, Doxepin, Fluacizine, Imipramine, Imipramine N-Oxide, Iprindole, Lofepramine, Melitracen, Metapramine, Nortriptyline, Noxiptilin, Opipramol, Propizepine, Protriptyline, Quinupramine, Tianeptine, Trimipramine Others such as Benactyzine, Bupropion, Butacetin, Deanol, Deanol Aceglumate, Deanol Acetamidobenzoate, Dioxadrol, Etoperidone, Febarbamate, Femoxetine, Fenpentadiol, Fluoxetine, Fluvoxamine, Hematoporphyrin, Hypercinin, Levophacetoperane, Lithium, Medifoxamine, Minaprine, Moclobemide, Oxaflozane, Piberaline, Polycyclic Imides, Prolintane, Pyrisuccideanol, Rubidium, Sulpiride, Sultopride, Teniloxazine, Thozalinone, Tofenacin, Toloxatone, Tranylcypromine, L-Tryptophan, Viloxazine, Zimeldine ANTIDIABETIC
Biguanides such as Buformin, Metformin, Phenformin
Sulfonylurea Derivatives such as Acetohexamide, 1-Butyl-3-metanilylurea, Carbutamide, Chlorpropamide, Glibornuride, Gliclazide, Glimepiride, Glipizide, Gliquidone, Glisoxepid, Glyburide, Glybuthiazol(e), Glybuzole, Glyhexamide, Glymidine, Glypinamide, Phenbutamide, Tolazamide, Tolbutamide, Tolcyclamide
Others such as Acarbose, Benzylthiazolidene-2,4-dione, Calcium Mesoxalate, Miglitol ANTIDIARRHEAL such as Acetyltannic Acid, Albumin Tannate, Alkofanone, Aluminum Salicylates, Catechin, Difenoxin, Diphenoxylate, Lidamidine, Loperamide, Mebiquine, Trillium, Uzarin ANTIDIURETIC such as Desmopressin, Felypressin, Lypressin, Ornipressin, Oxycinchophen, Terlipressin, Vasopressin ANTIESTROGEN such as Delmadinone Acetate, Ethamoxytriphetol, Tamoxifen, Toremifene ANTIFUNGAL (ANTIBIOTICS)
Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin
Others such as Azaserine, Griseofulvin, Pyrrolnitrin, Siccanin, Tubercidin, Viridin ANTIFUNGAL (SYNTHETIC)
Allylamines such as Naftifine, Terbinafine
Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole Nitrate, Sulconazole, Tioconazole
Triazoles such as Fluconazole, Itraconazole, Terconazole
Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionates, Propionic Acid, Pyrithione, Salicylanilide, Sulbentine, Tenonitrozole, Tolciclate, Tolindate, Tolnaftate, Tricetin, Ujothion, Undecylenic Acid ANTIGLAUCOMA such as Dapiprazoke, Dichlorphenamide, Dipivefrin, Pilocarpine ANTIGONADOTROPIN such as Danazol, Gestrinone, Paroxypropione ANTIGOUT such as Colchicine, Probenecid, Sulfinpyrazone ANTIHISTAMINIC
Alkylamine Derivatives such as Acrivastine, Bamipine, Brompheniramine, Chlorpheniramine, Dimethindene, Metron S, Pheniramine, Pyrrobutamine, Thenaldine, Tolpropamine, Triprolidine
Aminoalkyl Ethers such as Bietanautine, Bromodiphenhydramine, Carbinoxamine, Clemastine, Diphenlypyraline, Doxylamine, Embrammine, Medrylamine, Mephenphydramine, p-Methyldiphenhydramine, Orphenadrine, Phenyltoloxamine, Piprinhydrinate, Setasine
Ethylenediamine Derivatives such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine, Tripelennamine, Zolamine
Piperazines such as Cetirizine, Chlorcyclizine, Clocinizine, Hydroxyzine
Tricyclics
Phenothiazines such as Ahistan, Etymemazine, Fenethazine, N-Hydroxyethylpromethazine, Isopromethazine, Mequitazine, Promethazine, Pyrathiazine, Thiazinamium Methyl Sulfate
Others such as Azatadine, Clobenzepam, Cyproheptadine, Deptropine, Isothipendyl, Loratadine, Prothipendyl
Others such as Antazoline, Cetoxime, Clemizole, Clobenztropine, Diphenazoline, Diphenhydramine, Mebhydroline, Phenindamine, Terfenadine, Tritoqualine ANTIHYPERLIPOPROTEINEMIC
Aryloxyalkanoic Acid Derivatives such as Beclorbrate, Bazafibrate, Binifibrate, Ciprofibrate, Clinofibrate, Clofibrate, Clofibric Acid, Etonfibrate, Fenofibrate, Gemfibrozil, Nicofibrate, Pirifibrate, Ronifibrate, Simfibrate, Theofibrate
Bile Acid Sequesterants such as Cholestyramine Resin, Colestipol, Polidexide
HMG CoA Reductase Inhibitors such as Lovastatin, Pravastatin, Simvastatin
Nicotinic Acid Derivatives Aluminum Nicotinate, Acipimox, Niceritrol, Nicoclonate, Nicomol, Oxiniacic Acid
Thyroid Hormones/Analogs such as Etiroxate, Thyropropic Acid
Others such as Acifran, Azacosterol, Benfluorex, β-Benzalbutyramide, Benzodioxole, Carnitine, Chondroitin Sulfate, Clomestone, Detaxtran, Dextran Sulfate Sodium, 5,8,11,14,17-Eicosapentaenoic Acid, Eritadenine, Farnesylated tetrahydronaphthalenols, Furazbol, Meglutol, Melinamide, Mytatrienediol, Naphtyl-tetrahydronaphtyl-diphosphonates, Ornithine, γ-Oryzanol, Pantethine, Penataerythritol Tetraacetate, α-Phenylbutyramide, Phylate Acids and Salts, Pirozadil, Probucol, α-Sitosterol, Sultosilic Acid, Tiadenol, Triparanol ANTIHYPERTENSIVE
Benzothiadiazine Derivatives such as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide, Meticrane, Metolazone, Paraflutizide, Polythiazide, Tetrachlormethiazide, Trichlormethiazide N-Carboxyalkyl (peptide/lactam) Derivatives such as Alacepril, Captopril, Cilazapril, Delapril, Enalapril, Enalaprilat, Fosinopril, Lisinopril, Moveltipril, Perindopril, Quinapril, Ramipril Guanidine Derivatives Bethanidine, Debrisoquin, Guanacline, Guanadrel, Guanazodine, Guanethidine, Guanochlor, Guanoxabenz, Guanoxan Hydrazines/Phthalazines such as Cadralazine, Dihydralazine, Endralazine, Hydracarbazine, Hydralazine, Pheniprazine, Pildralazine, Todralazine Imidazole Derivatives such as Lofexidine, Phentolamine, Tolonidine Quaternary Ammonium Compounds Azamethonium, Chlorisondamine, Hexamethonium, Pentacynium Bis(methyl sulfate), Pentamethonium, Pentolinium Tartate, Phenactopinium, Trimethidiunum Methosulfate Quinazoline Derivatives such as Alfuzosin, Bunazosin Reserpine Derivatives such as Bietaserpine, Deserpidine, Rescinnamine, Reserpine, Syrosingopine Sulfonamide Derivatives such as Ambuside, Clopamide, Furosemide, Indapamide, Quinethazone, Tripamide, Xipamide Others such as Ajmaline, γAminobutyric Acid, Bufeniode, Chlorthalidone, Cicletaine, Ciclosidomine, Cryptenamine Tannates, Flosequinan, Indoramin, Ketanserin, Metbutamate, Mecamylamine, Methyldopa, Methyl 4-Pyridyl Ketone Thiosemicarbarzone, Metolazone, Minoxidil, Muzolimine, Pargyline, Pempidine, Pinacidil, Piperoxan, Primaperone, Propargyl Glycine Aminopropargyl Diols, Protoveratrines, Raubasine, Rescimetol, Saralasin, Sodium Nitroprusside, Ticrynafen, Trimethaphan Camsylate, Tyrosinase, Urapidil ANTIHYPERTHYROID such as 2-Amino-4-methylthiazole, 2-Aminothiazole, Carbimazole, 3,5-Dibromo-L-tyrosine, 3,5-Diiodotyrosine, Hinderin, Iodine, Iothiouracil, Methimazole, Methylthiouracil, Propylthiouracil, Sodium Perchlorate, Thibenzazoline, Thiobarbital, 2-Thiouracil ANTIHYPOTENSIVE such as Amezinium Methyl Sulfate, Angiotensin Amide, Etifelmin, Etilefrin, Gepefrine ANTIHYPOTHYROID such as Levothyroxine, Liothyronine, Thyroid, Thyroidin, Thyroxine, Tiratricol ANTI-INFLAMMATORY (NONSTEROIDAL)
Aminoarylcarboxylic Acid Derivatives such as Etofenamate, Meclofenamic Acid, Mefanamic Acid, Niflumic Acid Arylacetic Acid Derivatives such as Acemetacin, Amfenac, Cinmetacin, Clopirac, Diclofenac, Fenclofenac, Fenclorac, Fenclozic Acid, Fentiazac, Glucametacin, Isoxepac, Lonazolac, Metiazinic Acid, Oxametacine, Proglumetacin, Sulindac, Tiaramide, Tolmetin Arylbutyric Acid Derivatives such as Butibufen, Fenbufen Arylcarboxylic Acids such as Clidanac, Ketorolac, Tinoridine Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid, Tiaprofenic Acid Pyrazoles such as Mepirizole Pyrazolones such as Clofezone, Feprazone, Mofebutazone, Oxyphenbutazone, Phenylbutazone, Phenyl Pyrazolidininones, Suxibuzone, Thiazolinobutazone Salicylic Acid Derivatives such as Bromosaligenin, Fendosal, Glycol Salicylate, Mesalamine, 1-Naphthyl Salicylate, Olsalazine, Sulfasalazine Thiazinecarboxamides such as Droxicam, Isoxicam, Piroxicam Others such as ε-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocylic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4,6-di-tertiary-butyl-s-hydroxy-1,3-pyrimidines, Proquazone, Sialyl Lewis$^x$ Dimers, Tenidap ANTIMALARIAL such as Acedapsone, Alphaaminoquinolines, 4-Aminoquinolines, Amodiaquin, Arteether, Artemether, Artemisinin, Artesunate, Bebeerine, Berberine, Chirata, Chlorguanide, Chloroquine, Chlorproguanil, Cinchona, Cinchonidine, Cinchonine, Cycloguanil, Euquinine, Gentiopicrin, Halofantrine, Mefloquine Hydrochloride, 3-Methylarsacetin, Pamaquine, Plasmocid, Primaquine, Pyrimethamine, Quinacrine, Quinine (Acids, Salts and Derivatives), Quinine Formate, Quinine Gluconate, Quinine Tannate, Quinine Urea Hydrochloride, Quinocide, Quinoform, Quinoline, Sodium Arsenate, Diabasic ANTIMIGRAINE such as Alpiropride, Dihydroergotamine, Ergocornine, Ergocorninine, Ergocryptine, Ergot, Ergotamine, Flumedroxone Acetate, Fonazine, Methysergid(e), Oxetorone, Pizotyline, Sumatriptan ANTINAUSEANT such as Acetylleucine Monoethanolamine, Bietanautine, Bromopride, Buclizine, Clebopride, Cyclizine, Dimenhydrinate, Dipheniodol, Domperidone, Granisetron, Meclizine, Methalltal, Metoclopramide, Metopimazine, Nabilone, Ondansteron, Oxypendyl, Pipamazine, Piprinhydrinate, Scopolamine, Tetrahydrocannabinols, Thiethylperazine, Trimethobenzamide ANTINEOPLASTIC
Alkylating agents
Alkyl Sulfonates such as Busulfan, Improsulfan, Piposulfan Aziridines such as Benzodepa, Carboquone, Meturedepa, Uredepa Ethylenimines and Methylmelamines such as Altretamine, Triethylenemelamine, Triethylenephosphoramide, Triethylenethiophosphoramide, Trimethylolomelamine Nitrogen Mustards such as Chlorambucil, Chlornaphazine, Chclophosphamide, Estramustine, Ifosfamide, Mechlorethamine, Mechlorethamine Oxide Hydrochloride, Melphalan, Novembichin, Phenesterine, Prednimustine, Trofosfamide, Uracil Mustard Nitrosoureas Carmustine, Chlorozotocin, Fotemustine, Lomustine, Nimustine, Ranimustine Others such as Dacarbazine, Mannomustine, Mitobronitol, Mitolactol, Pipobroman Antibiotics such as Aclacinomycins, Actinomycin $F_1$, Anthramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, Plicamycin, Porfiromycin, Puromycin, Streptonigrin, Streptozocin, Tubercidin, Ubenimex, Zinostatin, Zorubicin Antimetabolites
- Folic Acid Analogs such as Denopterin, Methotrexate, Pteropterin, Trimetrexate
- Purine Analogs such as Fludarabine, 6-Mercaptopurine, Thiamiprine, Thioguanaine
- Pyrimidine Analogs such as Ancitabine, Azacitidine, 6-Azauridine, Carmofur, Cytarabine, Dideoxyuridines, Doxifluridine, Enocitabine, Floxuridine, Fluororacil, Tegafur Enzymes such as L-Asparaginase, Pulmozyme Others such as Aceglatone, Aldophophamide Glycoside, Aminolevulinic Acid, Amsacrine, Bestrabucil, Bisantrene, Carboplatin, Cisplatin, Defofamide, Demecolcine, Diaziquone, Elfornithine, Elliptinium Acetate, Etoglucid, Etoposide, Gallium Nitrate, Hydroxyurea, Interferon-$\alpha$, Interferon-$\beta$, Interferon-$\gamma$, Interleukine-2, Lentinan, Lonidamine, Mitoguazone, Mitoxantrone, Mopidamol, Nitracrine, Pentostatin, Phenamet, Pirarubicin, Podophyllinicc Acid, 2-Ethythydrazide, Procarbazine, PSK®, Razoxane, Sizofiran, Spirogermanium, Taxol, Teniposide, Tenuazonic Acid, Triaziquone, 2,2', 2,"-Trichlorotriethylamine, Urethan, Vinblastine, Vincristine, Vindesine ANTINEOPLASTIC (HORMONAL)
- Androgens such as Calusterone, Dromostanolone Propionate, Epitiostanol, Mepitiostane, Testolactone
- Antiadrenals such as Aminoglutethimide, Mitotane, Trilostane,
- Antiandrogens such as Flutamide, Nilutamide
- Antiestrogens such as Aromatase Inhibiting 4(5)-Imidazoles ANTINEOPLASTIC ADJUNCT
- Folic Acid Replenisher such as Frolinic Acid ANTIPARKINSONIAN such as Amantadine, Benserazide, Bietanautine, Biperiden, Budipine, Carbidopa, Deprenyl, Dexetimide, Diethazine, Droxidopa, Ethopropazine, Ethylbenzhydramine, Levodopa, Piroheptine, Pridinol, Prodipine, Terguride, Tiapride, Tigloidine ANTIPHEOCHROMOCYTOMA such as Metyrosine, Phenoxybenzamine ANTIPNEUMOCYSTIS such as Effornithine ANTIPROSTATIC HYPERTROPHY such as Proscar®

ANTIPROTOZOAL (LEISHMANIA) such as Ethylstibamine, Hydroxystilbamidine, N-Methylglucamine, Pentamidine, Stilbamidine ANTIPROTOZOAL (TRICHOMONAS) such as Acetarsone, Aminitrozole, Anisomycin, Azanidazole, Forminitrazole, Furazolidone, Hachimycin, Lauroguadine, Metronidazole, Nifuratel, Nimorazole, Silver Picrate, Tenonitrozole ANTIPROTOZOAL (TRYPANOSOMA) such as Benznidazole, Eflornithine, Melarsoprol, Nifurtimox, Oxophenarsine, Puromycin, Quinapyramine, Suramin Sodium, Trypan Red, Tryparasmide ANTIPRURITIC such as Camphor, Cyproheptadine, Dichlorisone, Glycine, Halometasone, 3-Hydroxycamphor, Menthol, Mesulphen, Methdilazine, Phenol, Spirit of Camphor, Trimeprazine ANTIPSORIATIC such as Acitretin, Anthralin, 6-Azauridine, Bergapten(e), Chrysarobin, Etretinate, Pyrogallol ANTIPSYCHOTIC
- Butyrophenones such as Benperidol, Bromperidol, Droperidol, Fluanisone, Haloperidol, Melperone, Moperone, Pipamperone, Sniperone, Timiperone, Trifluperidol
- Phenothiazines such as Acetophenazine, Butaperazine, Carphenazine, Chlorproethazine, Chlorpromazine, Clospirazine, Cyamemazine, Dixyrazine, Fluphenazine, Imiclopazine, Mepazine, Mesoridazine, Methoxypromazine, Metofenazate, Oxaflumazine, Perazine, Pericyazine, Perimethazine, Perphenazine, Piperacetazine, Pipotiazine, Prochlorperazine, Promazine, Sulforidazine, Thiopropazate, Thioridazine, Trifluoperazine, Triflupromazine
- Thioxanthenes such as Chlorprothixene, Clopenthixol, Flupentixol, Thiothixene
- Other Tricyclics such as Benzquinamide, Carpipramine, Clocapramine, Clomacran, Clothiapine, Clozapine, Opipramol, Prothipendyl, Tetrabenazine, Zotepine
- Others such as Alizapride, Amisulpride, 4-Arylpiperazines, 4-Arylpiperdines, Buramate, Fluspirilene, Molindone, Penfluridol, Pimozide, Spirilene, Sulpiride ANTIPYRETIC such as Aconine, Aconite, Aconitine, Phenicarbazide ANTIRICKETTSIAL such as p-Aminobenzoic Acid ANTISEBORRHEIC such as 3-O-Lauroylpyridoxol Diacetate, Piroctone, Resorcinol, Selenium Sulfides, Tioxolone ANTISEPTIC
- Guanidines such as Alexidine, Ambazone, Chlorhexidine, Picloxydine
- Halogens/Halogen Compounds such as Bornyl Chloride, Calcium Iodate, Iodine, Iodine Monochloride, Iodine Trichloride, Iodoform, Povidone-Iodine, Sodium Hypochlorite, Sodium Iadate, Symclosene, Thymol Iodide, Triclocarban, Triclosan, Troclosene Potassium
- Nitrofurans such as Furazolidone, 2-(Methoxymethyl)-5-Nitrofuran, Nidroxyzone, Nifuroxime, Nifurzide, Nitrofurazone
- Phenols such as Acetomeroctol, Chloroxylenol, Hexachlorophene, 1-Napthyl Salicylate, 2,4,6-Tribromo-m-cresol, 3', 4', 5-Trichloro-salicylanilide
- Quinolines such as Aminoquinuride, Chloroxine, Chlorquinaldol, Cloxyquin, Ethylhydrocupreine, Halquinol, Hydrastine, 8-Hydroxquinoline Sulfate
- Others such as Boric Acid, Chloroazodin, m-Cresyl Acetate, Cupric Sulfate, Ichthammol ANTISPASMODIC such as Alibendol, Ambucetamide, Aminopromazine, Bietamiverine, Butaverine, Butropium, Caroverine, Cimetropium, Cinnamedrine, Clebopride, Coniine Hydrobromide, Coniine, Difemerine, Diisopromine, Dioxaphetyl Butyrate, Drofenine, Ethaverine, Feclemine, Fenalamide, Fenoverine, Fenpiprane, Flavoxate, Flopropione, Gluconic Acid, Guaiactamine, Hydramitrazine, Hymecromone, Leiopyrrole, Mebeverine, Moxaverine, Nafiverine, Octaverine, Phenamacide, Phloroglucinol, Pinaverium, Piperilate, Pipoxolan Hydrochloride, Pramiverin, Properidine, Propivane, Propyromazine, Prozapine, Racefemine, Rociverine, Spasmolytol, Stilonium, Tiropramide, Trepibutone, Tricromyl, Trifolium, Trimebutine, N,N-1Trimethyl-3, 3-diphenyl-propylamine ANTITHROMBOTIC such as Anagrelide, Argatroban, Cilostazol, Daltroban, Defibrotide, Enoxaparin, Fraxiparine®, Indobufen, Lamoparan, Ozagrel, Picotamide, Plafibride, Tedelparin, Ticlopidine, Triflusal ANTITUSSIVE such as Allocamide, Amicibone, Benproperine, Benzonatate, Bibenzonium, Bromoform, Butamirate, Butethamate, Caramiphen Ethanedisulfonate, Carbetapentane, Chlophedianol, Clobutinol, Cloperastine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Enol Acetate, Dimemorfan, Dimethoxanate, α,α-Diphenyl-2-piperidinepropanol, Dropropizine, Drotebanol, Eprazinone, Ethyl Dibunate, Ethylmorphine, Fominoben, Guaiapate, Hydrocodone, Isoaminile, Levopropoxyphene, Morclofone, Narceine, Normethadone, Noscapine, Oxeladin, Oxolamine, Pholcodine, Picoperine, Pipazethate, Piperidione, Prenoxdiazine, Racemethorphan, Taziprinone Hydrochloride, Tipepidine, Zipeprol ANTIULCERATIVE such as Aceglutamide Aluminum Complex, ε-Acetamidocaproic Acid Zinc Salt, Acetoxolone, Arbaprostil, Benexate Hydrochloride, Bismuth Subcitrate Sol (Dried), Carbenoxolone, Cetraxate, Cimetidine, Enprostil, Esaprazole, Famotidine, Ftaxilide, Gefarnate, Guaiazulene, Irsogladine, Nizatidine, Omeprazole, Ornoprostil, γ-Oryzanol, Pifarnine, Pirenzepine, Plaunotol, Ranitidine, Rioprostil, Rosaprostol, Rotraxate, Roxatidine Acetate, Sofalcone, Spizofurone, Sucralfate, Teprenone, Trimoprostil, Thrithiozine, Troxipide, Zolimidine ANTIUROLITHIC such as Acetohydroxamic Acid, Allopurinol, Potassium Citrate, Succinimide ANTIVENIN such as Lyovac® Antivenin ANTIVIRAL
  Purines/Pyrimidinones such as 2-Acetyl-pyridine 5-((2-pyridylamino) thiocarbonyl) Thiocarbonohydrazone, Acyclovir, Dideoxyadenosine, Dideoxycytidine, Dideoxyinosine, Edoxudine, Floxuridine, Ganciclovir, Idoxuridine, MADU, Pyridinone, Trifluridine, Vidrarbine, Zidovudiine
  Others such as Acetylleucine Monoethanolamine, Acridinamine, Alkylisooxazoles, Amantadine, Amidinomycin, Cuminaldehyde Thiosemicarbzone, Foscarnet Sodium, Kethoxal, Lysozyme, Methisazone, Moroxydine, Podophyllotoxin, Ribavirin, Rimantadine, Stallimycin, Statolon, Thymosins, Tromantadine, Xenazoic Acid ANXIOLYTIC
  Arylpiperazines such as Buspirone, Gepirone, Ipsapirone
  Benzodiazepine Derivatives Alprazolam, Bromazepam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam, Tofisopam
  Carbamates such as Cyclarbamate, Emylcamate, Hydroxyphenamate, Meprobamate, Phenprobamate, Tybamate
  Others Alpidem, Benzoctamine, Captodiamine, Chlormezanone, Etifoxine, Fluoresone, Glutamic Acid, Hydroxyzine, Mecloralurea, Mephenoxalone, Oxanamide, Phenaglycodol, Suriclone BENZODIAZEPINE ANTAGONIST such as Flumazenil BRONCHODILATOR
  Ephedrine Derivatives such as Albuterol, Bambuterol, Bitolterol, Carbuterol, Clenbuterol, Clorprenaline, Dioxethedrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Soterenol, Terbutaline, Tulobuterol
  Quaternary Ammonium Compounds such as Clutropium Bromide, Oxitropium Bromide
  Xanthine Derivatives such as Acefylline, Acefylline Ambuphylline, Aminophylline, Bamifylline, Choline Theophyllinate, Doxofylline, Dyphylline, Enprofylline, Etamiphyllin, Etofylline, Guaithylline, Proxyphylline, Theobromine, 1-Theobromineacetic Acid, Theophylline
  Others such as Methoxyphenanime, Tretoquinol CALCIUM CHANNEL BLOCKER
  Arylalkylamines such as Bepridil, Ditiazem, Fendiline, Gallopamil, Terodiline, Verapamil
  Dihydropyridine Derivatives such as Felodipine, Isradipine, Nicardipine, Nifedipine, Nilvadipine, Nimodipine, Nisoldipine, Nitrendipine
  Piperazine Derivatives such as Flunarisine
  Others such as Perhexiline CALCIUM REGULATOR such as Calcifediol, Calcitonin, Calcitriol, Clodronic Acid, Dihydrotachysterol, Elcatonin, Etidronic Acid, Ipriflavone, Pamidronic Acid, Parathyroid Hormone, Teriparatide Acetate CARDIOTONIC such as Acetyldigititoxins, 2-Amino-4-picoline, Amrinone, Buclasdesine, Cerberoside, Camphotamide, Convallatoxin, Cymarin, Denopamine, Deslanoside, Ditalin, Digitalis, Digitoxin, Digoxin, Dobutamine, Dopamine, Dopexamine, Enoximone, Erythrophleine, Fenalcomine, Gitalin, Gitoxin, Glycocyamine, Heptaminol, Hydrastinine, Lanotodises, Metamivam, substituted Methoxyphenyl-4, 5-dihydro-3(2H)-pridazinones, Milrinone, Neriifolin, Oleandrin, Ouabain, Oxyfedrine, Prenalterol, Proscillaridin, Resibufogenin, Scillaren, Scillarenin, Strophanthin, Sulmazole, Theobromine, Xamoterol CHELATING AGENT such as Deferozmine, Edetate Calcium Disodium, Edetate Disodium, Edeate Sodium, Edetate Trisodium, Pentetate Calcium Trisodium, Pentectic Acid, Succimer, Trientine CHOLECYSTOKININ ANTAGONIST (CCK Antagonist)

CHOLELITHOLYTIC AGENT such as Chenodiol, Methyl tert-Butyl Ether, Monooctanoin, Ursodiol CHOLERETIC such as Alibendol, Anethole Trithion, Azintamide, Cholic Acid, Cicrotoic Acid, Clanobutin, Cyclobutyrol, Cyclovalone, Cynarin(e), Dehydrocholic Acid, Deoxycholic Acid, Dimecrotic Acid, α-Ethylbenzyl Alcohol, Exiproben, Feguprol, Fencibutirol, Fenipentol, Florantyrone, Hymecromone, Menbutone, 3-(O-Methoxyphenyl)-2-phenylacrylic Acid, Metochalcone, Moquizone, Osalmid, Ox Bile Extract, 4, 4'-Oxydi-2-butanol, Piprozolin, Prozapine, 4-Salicyloylmorpholine, Sincalide, Taurocholic Acid, Timonacic, Tocamphyl, Trepibutone, Vanitiolide CHOLINERGIC such as Aceclidine, Acetylcholine, Acetylcholide, Aclatonium Napadisilate, Benzpyrinium Bromide, Bethanechol, Carbachol, Carpronium, Demecarium, Dexpanthenol, Diisopropyl Paraoxon, Echothiophate, Edrophomium, Eseridine, Furtrethonium, Isoflurophate, Methacholine Chloride, Muscarine, Neostigmine, Oxapropanium, Physostigmine, Pyridostigmine CHOLINESTERASE INHIBITOR such as Ambenonium, Distigmine, Galanthamine CHOLINESTERASE REACTIVATOR such as Obidoximine, Pralidoxime CNS STIMULANT/AGENT such as Amineptine, Amphetimine, Amphetaminil, Bemegride, Benzphetamine, Brucine, Caffeine, Chlorphentermine, Clofenciclan, Clortermine, Coca, Demanyl Phosphate, Dexoxadrol, Dextroamphetamine Sulfate, Diethlpropion, N-Ethylamphetamine, Ethamivan, Etifelmin, Etryptamine, Fencamfamine, Fenethylline, Fenosolone, Flurothyl, Hexacyclonate Sodium, Homocamfin, Mazindol, Megexamide, Methamphetamine, Methylphenidate, Nicotine, Nicotinic Agonist, Nikethamide, Pemoline, Pentylenetetrazole, Phenidimetrazine, Phenmetrazine, Phentermine, Picrotoxin, Pipradrol, Prolintane, Pyrovalerone, Tetrahydrobenzothienopyridines DECONGESTANT such as Cafaminol, Nordefrin DENTAL CARRIES PROPHYLACTIC such as Sodium Fluoride DEPIGMENTOR such as Hydroquinine, Hydroquinone, Monobenzone DIURETIC
Organomercurials such as Chlormerodrin, Meralluride, Mercamphamide, Mercaptomerin Sodium, Mercumallylic Acid, Mercumatilin Sodium, Mercurous Chloride, Mersalyl
Pteridines such as Furterene, Triamterene
Purines such as 7-Morpholinomethyltheophylline, Pamabrom, Protheobromine, Theobromine
Steroids such as Canrenone, Oleandrin, Spironolactone
Sulfonamide Derivatives such as Acetazolmide, Azosemide, Bumetanide, Butazolamide, Chloraminophenamide, Clofenamide, Clorexolene, Diphenylmethane-4, 4'-disulfonamide, Disulfamide, Ethoxzolamide, Flumethiazide, Mefruside, Methazolamide, Piretanide, Torasemide
Uracils such as Aminometradine, Amisometradine
Others such as Amanozine, Amiloride, Arbutin, Chlorazanil, Ethacrynic Acid, Etozolin, Isosorbide, Mannitol, Metochalcone, Perhexiline, Urea DOPAMINE RECEPTOR AGONIST such as Bromocriptine, Fenoldopam, Lisuride, Naxagolide, Pergolide ECTOPARASITICIDE such as Amitraz, Benzyl Benzoate, Carbaryl, Crotamiton, DDT, Dixanthogen, Isobornyl Thiocyanoacetate (Technical), Lime Sulfurated Solution, Lindane, Malathion, Mercuric Oleate, Sulphur (pharmaceutical)

ENZYME
Digestive such as α-Amylase (Swine Pancreas), Lipase, Pancrelipase, Pepsin, Rennin
Penicillin Inactivating such as Penicillinase
proteolytic such as Collagenase, Chymopapain, Chymotrypsins, Papain, Trypsin ENZYME INDUCER (HEPATIC) such as Flumecinol ESTROGEN
Nonsteroidal such as Benzestrol, Broparoestrol, Chlorotrianisene, Dienestrol, Diethylstilbestrol, Diethylstilbestrol Diproprionate, Dimestrol, Fosfestrol, Hexestrol, Methallenestril, Methestrol
Steroidal such as Colpormon, Conjugated Estrogenic Hormones, Equilenin, Equilin, Esterified Estrogens, Esteropipate, 17β-Estradiol, Estradiol, Estradiol Benzoate, Estradiol 17β-Cypionate, Estriol, Estrone, Ethinyl Estradiol, Mestranol, Moxestrol, Mytatrienediol, Polyestradiol Phosphate, Quinestradiol, Quinestrol GASTRIC SECRETION INHIBITOR such as Enterogastrone, Octreotide GLUCOCORTICOID such as 21-Acetoxyprefnenolone, Aalclometasone, Algestone, Amicinonide, Beclomethasone, Betamethasone, Betamethasone Dipropionate, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumehtasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Formocortal, Halcinonide, Halometasone, Halopredone Acetate, Hydrocortamate, Hydrocortisone, Hydrocortisone Acetate, Hydrocortisone Phosphate, Hydrocortisone 21-Sodium Succinate, Hydrocortisone Tebutate, Mazipredone, Medrysone, Meprednisone, Methyolprednisolone, Mometasone Furoate, Paramethasone, Prednicarbate, Prednisolone, Prednisolone 21-Diethylaminoacetate, Prednisone Sodium Phosphate, Prednisolone Sodium Succinate, Prednisolone Sodium 21-m-Sulfobenzoate, Prednisolone 21-Stearoylglycolate, Prednisolone Tebutate, Prednisolone 21-Trimethylacetate, Prednisone, Prednival, Prednylidene, Prednylidene 21-Diethylaminoacetate, Tixocortal, Triamcinolone, Triamcinolone Acetonide, Triamcinolone Benetonide, Triamcinolone Hexacetonide GONAD-STIMULATING PRINCIPLE such as Clomiphene, Cyclofenil, Epimestrol, FSH, HCG, LH-RH GONADOTROPIC HORMONE such as LH, PMSG GROWTH HORMONE INHIBITOR such as Somatostatin GROWTH HORMONE RELEASING FACTOR such as Semorelin GROWTH STIMULANT such as Somatotropin HEMOLYTIC such as Phenylhydrazine HEPARIN ANTAGONIST such as Hexadimethrine, Protamines HEPATOPROTECTANT such as Betaine, Citolone, Malotilate, Orazamide, Phosphorylcholine, Protoporphyrin IX, Silymarin-Group, Thiotic Acid IMMUNOMODULATOR such as Amiprilose, Bucillamine, Ditiocarb Sodium, Inosine Pranobex, Muroctasin, Platonin, Procodazole, Tetramisole, 6-aryl-5, 6-dihydroimidazol-(2, 1-B) Thiazole Derivatives, Thymomodulin, Thymopentin IMMUNOSUPPRESSANT such as Cyclophilin, Cyclosporins, FK-506, Mizoribine, Rapamycin, Rapamycin Sulfamates ION EXCHANGE RESIN such as Carbacrylic Resins, Resodec, Sodium Polystyrene Sulfonate LACTATION STIMULATING HORMONE such as Prolactin LH-RH AGONIST such as Buserelin, Goserelin, Leuprolide, Nafarelin, Triptorelin LIPOTROPIC such as N-Acetylmethionine, Choline Chloride, Choline Dehydrocholate, Choline Dihydrogen Citrate, Inositol, Lecithin, Methionine LUPUS ERYTHEMATOSUS SUPPRESSANT such as Bismuth Sodium Triglycollamate, Bismuth Subsalicylate MINERALOCORTICOID such as Aldosterone, Deoxycorticosterone, Fludrocortisone MIOTIC such as Pilocarpus MONOAMINE OXIDASE INHIBITOR such as Phenoxypropazine, Pivalylbenzhydrazine MUCOLYTIC such as Acetylcysteine, Bromhexine, Carbocysteine, Domiodol, Letosteine, Mecysteine, Mesna, Sobrerol, Stepronin, Tiopronin, Tyloxapol MUSCLE RELAXANT (SKELETAL) such as Afloqualone, Alcuronium, Atracurium Besylate, Baclofen, Benzoquinonium, C-Calebassine, Carisoprodol, Chlorphenesin Carbamate, Chlozoxazone, Curate, Cyclobenzaprine, Dantrolene, Decamethonium, Eperisone, Fazadinium, Flumetramide, Gallamine Triethiodide, Hexacarbacholine, Hexafluorenium, Idrocilamide, Lauexium Methyl Sulfate, Leptodactyline, Memantine, Mephenesin, Metaxalone, Methocarbamol, Metocurine Iodide, Pancuronium, Pipecurium, Promoxolane, Quinine Sulfate, Styramate, Succinylcholine, Succinylcholine Suxethonium Bromide, Tetrazepam, Thiocolchicoside, Tizanidine, Tolperisone, Tubocurarine, Vecuronium, Zoxolamine NARCOTIC ANTAGONIST such as Amiphenazole, Cyclazocine, Levallorphan, Nadide, Nalmafene, Nalorphine, Nalorphine Dinicotinate, Naloxone, Naltrexone NEUROPROTECTIVE such as Dizocilpine NOOTROPIC such as Aceglutamide, Acetylcarnitine, Aniracetam, Bifematlane, Exifone, Fipexide, Idebenone, Indeloxazine, Nizofenone, Oxiracetam, Piracetam, Propentofylline, Pyritinol OPHTHALMIC AGENT such as 15-ketoprostaglandins OVARIAN HORMONE such as Relaxin OXYTOCIC such as Carboprost, Cargutocin, Deaminooxytocin, Ergonovine, Gemeprost, Methylergonovine, Oxytocin, Pituitary (Posterior), Prostaglandin $E_2$, Prostaglandin $F_{2\alpha}$, Sparteine PEPSIN INHIBITOR such as Sodium Amylosulfate PERISTALTIC STIMULANT such as Cisapride PROGESTOGEN such as Allylestrenol, Anagestone, Chlormadinone Acetate, Delmadinone Acetate, Demegestone, Desogestrel, Dimethisterone, Dydrogesterone, Ethinylestrenol, Ethisterone, Ethynodiol, Ethynodiol Diacetate, Flurogestone Acetate, Gestodene, Gestonorone Caproate, Haloprogesterone, 17-Hydroxy-16-methylene-progesterone, 17α-Hydroxyprogesterone, 17α-Hydroxygesterone Caproate, Lynestrenol, Medrogestone, Medroxyprogesterone, Megestrol Acetate, Melengestrol, Norethindrone, Norethindrone Acetate, Norethynodrel, Norgesterone, Norgestimate, Norgestrel, Norgestrienone, 19-Norprogesterone, Norvinisterone, Pentagestrone, Progesterone, Promegestone, Quingestrone, Trengestone PROLACTIN INHIBITOR such as Metergoline PROSTAGLANDIN/PROSTAGLANDIN ANALOG such as Bemeprost, Prostacyclin, Prostaglandin $E_1$, Sulprostone PROTEASE INHIBITOR such as Aprotinin, Camostat, Gabexate, Nafamostat RESPIRATORY STIMULANT such as Almitrine, Dimefline, Dimorpholamine, Doxapram, Lobeline, Mepixanox, Pimeclone, Sodium Succinate, Tacrine SCLEROSING AGENT such as Ethanolamine, Ethylamine, 2-Hexyl-decanoic Acid, Sodium Ricinoleate, Sodium Tetradecyl Sulfate, Tribenoside

SEDATIVE/HYPNOTIC

Acyclic Ureides such as Acecarbromal, Apronalide, Bornisovalum, Capuride, Carbromal, Ectylurea Alcohols such as Chlorhexadol, Ethchlorvynol, 4-Methyl-5-thiazoleethanol, tert-Pentyl Alcohol, 2, 2, 2-Trichloroethanol Amides such as Butoctamide, Diethylbromoacetamide, Ibrotamide, Isovaleryl Diethylamide, Niaprazine, Tricetamide, Trimetozine, Zolpidem, Zopiclone Barbituric Acid Derivatives such as Allobarbital, Amobarbital, Aprobarbital, Barbital, Brallabarbital, Butabarbital Sodium, Butalbital, Butallylonal, Butethal, Carbubarb, Cyclobarbital, Cyclopentobarbital, Enallylpropymal, 5-Ethyl-5-(1-piperidyl) barbituric Acid, 5-Furfuryl-5-isopropylbarbituric Acid, Heptabarbital, Hexethal Sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetrabarbital, Vinbarbital Sodium, Vinylbital Benzodiazepine Derivatives such as Brotizolam, Doxefazepam, Estazolam, Flunitrazepam, Flurazepam, Haloxazolam, Loprazolam, Lormetazepam, Nitrazepam, Quazepam, Temasepam, Triazolam Bromides such as Ammonium Bromide, Calcium Bromide, Calcium Bromolactobionate, Lithium Bromide, Magnesium Bromide, Potassium Bromide, Sodium Bromide Carbamates such as Amyl Carbamate (Tertiary), Ethinamate, Hexaprpymate, Meparfynol Carbamate, Novonal, Tricholorourethan Chloral Derivatives such as Carbocloral, Chloral Betaine, Chloral Formamide, Chloral Hydrate, Chloralantipyrine, Dichloralphenazone, Pentaerythritol Chloral, Triclofos Piperidinediones such as Glutehimide, Methyprylon, Piperidione, Pyrithyldione, Taglutimide, Thalidomide Quinazolone Derivatives such as Etaqualone, Mecloqualone, Methaqualone Others such as Acetal, Acetophenone, Aldol, Ammonium Valerate, Amphenidone, d-Bornyl α-Bromoisovalerate, d-Bornyl Isovalerate, Bromoform, Calcium 2-Ethylbutanoate, Carfinate, α-Chlorolose, Clomethiazole, Cypripedium, Doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone, Sodium Oxybate, Sulfonethylmethane, Sulfonmethane THROMBOLYTIC such as APSAC, Plasmin, Pro-Urokinase, Streptokinase, Tissue Plasminogen Activator, Urokinase THYROTROPIC HORMONE such as TRH, TSH URICOSURIC such as Benzbromarone, Ethebenecid, Orotic Acid, Zoxazolamine VOSODILATOR (CEREBRAL) such as Bencyclane, Ciclonicate, Cinnarizine, Citicoline, Diisopropylamine Dichloractetate, Eburnamonine, Fenoxedil, Ibudilast, Ifenprodil, Nafronyl, Nicametate, Nicergoline, Nimodipine, Papaverine, Pentifylline, Tinofedrine, Vincamine, Vinpocetine VASODILATOR (CORONARY) such as Amotriphene, Bendazol, Benfurodil Hemisuccinate, Benziodcarone, Chloacizine, Chromonar, Clobenfurol, Clonitrate, Dilazep, Dipyridamole, Droprenilamine, Efloxate, Erythritol, Erythrityl Tetranitrate, Etafenone, Floredil, Ganglefene, Hexestrol Bis(β-diethylaminoethyl ether), Hexobendine, Isosorbitol Dinitrate, Itramin Tosylate, Khellin, Lidoflazine, Mannitol Hexanitrate, Medibazine, Nicorandil, Nitroglycerin, pentaerythritol Tetranitrate, Pentrinitrol, Pimefylline, Potassium Nitrite, Prenylamine, Propatyl Nitrate, Pyridofylline, Trapidil, Tricromyl, Trimetazidine, Trolnitrate Phosphate, Visnadine VASODILATOR (PERIPHERAL) such as Bamethan, Betahistine, Bradykinin, Brovincamine, Bufoniode, Buflomedil, Butalamine, Cetiedil, Ciclonicate, Cinepazide, Cyclandelate, Eledoisin, Heronicate, Inositol Niacinate, Isoxsuprine, Kallidin, Kallikrein, Moxisylyte, Nicofuranose, Nicotinyl Alcohol, Nylidrin, Pentoxifylline, Piribedil, Suloctidil, Xanthinal Niacinate VASOPROTECTANT such as Benzarone, Bioflavonoids, Chromocarb, Clobeoside, Diosmin, Dobesilate Calcium, Escin, Rolescutol, Leucocyanidin, Metescufylline, Quercetin, Rutin, Troxerutin VITAMIN/VITAMIN SOURCE/EXTRACTS such as Vitamins A, B, C, D, E, and K and derivatives thereof, Calciferols, Glycyrrhiza, Mecobalamin VULNERARY such as Allantoin, Asiaticoside, Cadexomer Iodine, Chitin, Dextranomer The above list of pharmaceutical agents is based upon the list provided in The Merk Index, 11th Edition, Merck & Co. Rahway, N.J. (1989). Moreover, the above drugs may be used either in the free form or, if capable of forming salts, in the form of a saly with a suitable acid or base; if the drug has a carboxyl group, its esters may also be employed.

What is claimed is:

1. A flexible, finite, bioadhesive composition for topical application comprising:

(a) a therapeutically effective amount of at least one pharmaceutically active agent;

(b) a pharmaceutically acceptable solvent for the pharmaceutically active agent and a plasticizer;

(c) in admixture with the pharmaceutically active agent in the solvent, a pharmaceutically acceptable bioadhesive carrier in an amount from about 5 to 50 percent based on the weight of the whole composition; and (d) a cohesive increasing amount of a clay;

wherein the composition is substantially free of water, substantially water insoluble and is a bioadhesive; and wherein the pharmaceutically active agent is present in non-crystallized form in the composition.

2. The composition of claim 1, wherein the pharmaceutically acceptable solvent is in an amount from about 20 to about 50 weight percent based on the weight of the whole composition, of which the plasticizer represents about 10 to about 30 weight percent based on the weight of the whole composition, the bioadhesive carrier is in an amount from about 20 to about 50 weight percent and the clay represents about 0.5 to 20% based on the weight of the whole composition.

3. The composition of claim 1, wherein the pharmaceutically active agent is at least one local anesthetic in an amount of about 10 to 40 weight percent based on the weight of the total composition.

4. The composition of claim 1, wherein the pharmaceutically active agent is from a class of drugs selected from the group consisting of analgesic anti-inflammatory drugs, central nervous system drugs, antihistaminic or antiallergic drugs, acitonide anti-inflammatory drugs, androgenic and estrogenic steroids, respiratory drugs, sympathomimetic drugs, antimicrobial drugs, antihypertensive drugs, cardiotonic drugs, coronary vasodilators, vasoconstrictors, beta blocking and antiarrhythemic drugs, calcium antagonistic and other circulatory anticonvulsants, anti-vertigo-tranquilizing drugs, antipsychotic drugs, muscle-reactants drugs, anti-Parkinson drugs, non-steroidal hormones, anti-hormones, vitamins, anti-tumor, enzymes, herb medicines or crude extracts, miotics, cholinergic agonists, antimuscarinic or muscarinic cholinergic blocking drugs, mydriatics, psychic energizers, humoral agents, antispasmodic drugs, antidepressants, antidiabetics, anorexic drugs, anti-allergic drugs, decongestants, antipyretics, anti-migraine drugs, antimalarial, antiulcer drugs, peptides, and anti-estrogens.

5. The composition of claim 4, in which the pharmaceutically active agent is one or more steroids selected from the group consisting of androgenic steroids, including testosterone; methyltestosterone; fluoxymesterone; estrogenic steroids, including conjugated estrogens, esterified estrogens, estropipate, 17β-estradiol, 17β-estradiol esters such as 17β-estradiol valerate, equilin, mestranol, estrone, estriol; 17β-estradiol derivatives such as 17β-ethinyl estradiol; diethylstilbestrol, progestational agents, including progesterone and progesterone analogs such as 19-norprogesterone, hydroxyprogesterone caproate, 17β-hydroxyprogesterone, dydrogesterone, medroxyprogesterone acetate; and norethindrone, norethindrone acetate, melengestrol, chlormadinone; ethynodiol diacetate, norethynodrel, dydrogesterone, dimethisterone, ethinylestrenol, norgestrel, demegestone, promegestone, megestrol acetate, anti-estrogen and anti-androgenic steroids.

6. The composition of claim 3, wherein the anesthetic agent is selected from the group consisting of procaine, lidocaine, prilocaine, mepivacaine, dyclonine, dibucaine, benzocaine, chloroprocaine, tetracaine, bupivacaine, and etidocaine and is in the form of the base or an acid-addition salt or both forms.

7. The composition of claim 6, wherein the acid-addition salt is hydrochloride.

8. The composition of claim 1, wherein the bioadhesive is selected from the group consisting of gums and celluloses.

9. The composition of claim 8, wherein the gum is selected from the group consisting of karaya gum, tragacanth gum, pectin gum, xanthan gum, guar gum, cellulose, and cellulose derivatives.

10. The composition of claim 3, wherein the solvent for the anesthetic agent is at least one polyhydric alcohol.

11. The composition of claim 10, wherein the polyhydric alcohol is a polyalkylene glycol.

12. The composition of claim 11, wherein the glycol is selected from the group consisting of dipropylene glycol, propylene glycol, ethylene glycol, polyethylene glycol, glycerin, butylene glycol, hexylene glycol, polypropylene glycol, and sorbitol.

13. The composition of claim 1 further comprising a backing material conforming to the size and shape of a single dosage of the composition.

14. The composition of claim 1 comprising about 20 to 35 weight percent of karaya gum, about 20 to 40 weight percent of at least one glycol, about 10 to 25 weight percent of lidocaine base, and 1 to 7 percent smectite clay, and further comprising a binder in an amount sufficient to bind the other ingredients.

15. The composition of claim 1 comprising about 10 weight percent of karaya gum, about 13 weight percent of at least one glycol, and about 8 weight percent of lidocaine base, and further comprising a binder in an amount sufficient to bind the other ingredients.

16. The composition of claim 1 comprising about 7 weight percent of karaya gum, about 13 weight percent of at least one glycol, and about 8 weight percent of lidocaine base, and further comprising a binder in an amount sufficient to bind the other ingredients.

17. The composition of claim 1 comprising about 5 weight percent of karaya gum, about 13 weight percent of at least one glycol, and about 8 weight percent of lidocaine base, 2 percent Bentonite, and further comprising a binder in an amount sufficient to bind the other ingredients.

18. The composition of claim 1 comprising about 5 weight percent of karaya gum, about 13 weight percent of at least one glycol, and about 8 weight percent of lidocaine base, 2 percent Bentonite, and further comprising a binder in an amount sufficient to bind the other ingredients.

19. The composition of claim 1, wherein the pharmaceutically active agent is an anti-microbial agent.

20. The composition of claim 19, wherein the anti-microbial agent in an antifungal agent.

21. The composition of claim 20, wherein the anti-microbial agent is clotrimazole.

22. The composition of claim 20, wherein the antimicrobial agent is miconazole.

23. A method of administering one or more pharmaceutically active agents to a subject comprising the steps of:

providing the composition set forth in claim 1; and contacting an area of skin or mucous membrane with the composition to administer the pharmaceutically active agent.

24. The method of claim 21, wherein the pharmaceutically active agent is an anesthetic agent selected from the group consisting of procaine, dyclonine, lidocaine, prilocaine, mepivacaine, benzocaine, propoxycaine, chloroprocaine, tetracaine, bupivacaine, etidocaine, and dibucaine.

25. The method of claim 22, wherein the anesthetic agent is administered in the form of a free base.

26. The method of claim 22, wherein the anesthetic agent is administered in the form of an acid-addition salt.

27. The method of claim 22, wherein the solvent is at least one polyhydric alcohol.

* * * * *